(12) United States Patent
Lozier et al.

(10) Patent No.: US 8,603,102 B2
(45) Date of Patent: Dec. 10, 2013

(54) BONE FIXATION TOOL

(75) Inventors: Antony J. Lozier, Warsaw, IN (US); Daniel P. Murphy, Claypool, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 13/493,200

(22) Filed: Jun. 11, 2012

(65) Prior Publication Data

US 2012/0253411 A1 Oct. 4, 2012

Related U.S. Application Data

(63) Continuation of application No. 12/787,518, filed on May 26, 2010, now Pat. No. 8,221,433.

(60) Provisional application No. 61/181,024, filed on May 26, 2009.

(51) Int. Cl.
*A61B 17/58* (2006.01)
*A61B 17/60* (2006.01)
*A61F 2/00* (2006.01)

(52) U.S. Cl.
USPC .......................................................... 606/104

(58) Field of Classification Search
USPC ............. 606/86 A, 99, 104, 914, 916; 81/436
See application file for complete search history.

(56) References Cited

U.S. PATENT DOCUMENTS

| | | | |
|---|---|---|---|
| 3,584,629 A | 6/1971 | Hoef et al. | |
| 3,618,842 A | 11/1971 | Bryan | |
| 3,662,939 A | 5/1972 | Bryan | |
| 3,752,161 A | 8/1973 | Bent | |
| 3,815,476 A | 6/1974 | Green et al. | |
| 3,842,839 A | 10/1974 | Malis et al. | |
| 3,905,276 A | 9/1975 | Noiles et al. | |
| 4,349,028 A | 9/1982 | Green | |
| 4,540,110 A | 9/1985 | Bent et al. | |
| 4,728,876 A | 3/1988 | Mongeon et al. | |
| 4,890,597 A | 1/1990 | Ekstrom | |

(Continued)

FOREIGN PATENT DOCUMENTS

| | | |
|---|---|---|
| EP | 0171967 A2 | 2/1986 |
| EP | 0171967 A3 | 2/1986 |

(Continued)

OTHER PUBLICATIONS

"3M Staplizer Powered Metaphyse", [Online]. Retrieved from the Internet: <URL: http://www.wemed1.com/Products/spec.asp?ItemNumber=OR-3M-T100&Code=zzor3mc100>, (Accessed Apr. 22, 2013), 1 pg.

(Continued)

*Primary Examiner* — Sameh Boles
(74) *Attorney, Agent, or Firm* — Schwegman, Lundberg & Woessner P.A.

(57) ABSTRACT

A tool and a method are provided for driving a bone pin into a fractured bone to stabilize the fractured bone by maintaining the fractured bone in a reduced state. The tool may be a handheld device including a cartridge having at least one passageway that receives the bone pin. The tool may also include a pneumatically-powered piston having a needle that is sized for receipt within the passageway of the cartridge, the needle applying sufficient force to the bone pin to drive the bone pin out of the cartridge and into the fractured bone.

13 Claims, 17 Drawing Sheets

(56) References Cited

U.S. PATENT DOCUMENTS

| | | |
|---|---|---|
| 4,901,712 A | 2/1990 | Voegell et al. |
| 4,909,419 A * | 3/1990 | Yamada et al. ............. 227/1 |
| 4,915,013 A | 4/1990 | Moraht et al. |
| 4,938,408 A | 7/1990 | Bedi et al. |
| 4,951,861 A | 8/1990 | Schulze et al. |
| 5,049,775 A | 9/1991 | Smits |
| 5,080,273 A | 1/1992 | Meyer |
| 5,086,749 A | 2/1992 | Ekstrom |
| 5,125,923 A | 6/1992 | Tanner et al. |
| 5,136,469 A | 8/1992 | Carusillo et al. |
| 5,149,603 A | 9/1992 | Fleming et al. |
| 5,160,795 A | 11/1992 | Milliman |
| 5,265,582 A | 11/1993 | Bhogal |
| 5,330,487 A | 7/1994 | Thornton et al. |
| 5,363,834 A | 11/1994 | Stuchlik |
| 5,366,459 A | 11/1994 | Yoon |
| 5,370,037 A | 12/1994 | Bauer et al. |
| 5,398,861 A | 3/1995 | Green |
| 5,400,536 A | 3/1995 | Milliman |
| 5,415,631 A | 5/1995 | Churinetz et al. |
| 5,431,322 A | 7/1995 | Green et al. |
| 5,485,887 A | 1/1996 | Mandanis |
| 5,497,758 A | 3/1996 | Dobbins et al. |
| 5,515,838 A | 5/1996 | Anderson |
| 5,613,483 A | 3/1997 | Lukas et al. |
| 5,628,444 A | 5/1997 | White |
| 5,664,552 A | 9/1997 | Kunimoto |
| 5,669,369 A | 9/1997 | Scott |
| 5,687,897 A | 11/1997 | Fa et al. |
| 5,704,150 A | 1/1998 | Milliman |
| 5,709,334 A | 1/1998 | Sorrentino et al. |
| 5,711,472 A | 1/1998 | Bryan |
| 5,755,213 A | 5/1998 | Gardner, Jr. et al. |
| 5,755,726 A | 5/1998 | Pratt et al. |
| 5,769,781 A | 6/1998 | Chappuis |
| 5,772,096 A | 6/1998 | Osuka et al. |
| 5,775,312 A | 7/1998 | Wilkinson et al. |
| 5,779,130 A | 7/1998 | Alesi et al. |
| 5,782,821 A | 7/1998 | Couch |
| 5,785,228 A | 7/1998 | Fa et al. |
| 5,803,733 A | 9/1998 | Trott et al. |
| 5,859,359 A | 1/1999 | Reid |
| 5,862,972 A | 1/1999 | Green et al. |
| 5,865,360 A | 2/1999 | White |
| 5,878,734 A | 3/1999 | Johnson et al. |
| 5,878,736 A | 3/1999 | Lotuaco, III |
| 5,896,933 A | 4/1999 | White |
| 5,911,722 A | 6/1999 | Adler et al. |
| 5,913,303 A | 6/1999 | Kotsiopoulos |
| 5,918,791 A | 7/1999 | Sorrentino et al. |
| 5,924,413 A | 7/1999 | Johnson et al. |
| 5,954,259 A | 9/1999 | Viola et al. |
| 5,954,689 A | 9/1999 | Poulsen |
| 5,957,119 A | 9/1999 | Perry et al. |
| 5,957,951 A | 9/1999 | Cazaux et al. |
| 5,989,214 A | 11/1999 | van de Wijdeven |
| 5,997,500 A | 12/1999 | Cook et al. |
| 6,006,704 A | 12/1999 | Phillips et al. |
| 6,010,508 A | 1/2000 | Bradley |
| 6,015,078 A | 1/2000 | Almeras et al. |
| 6,016,945 A | 1/2000 | Phillips et al. |
| 6,039,231 A | 3/2000 | White |
| 6,042,571 A | 3/2000 | Hjertman et al. |
| 6,059,749 A | 5/2000 | Marx |
| 6,197,041 B1 | 3/2001 | Shichman et al. |
| 6,223,658 B1 | 5/2001 | Rosa et al. |
| 6,286,497 B1 | 9/2001 | Levkov |
| 6,306,125 B1 | 10/2001 | Parker et al. |
| 6,371,099 B1 | 4/2002 | Lee |
| 6,371,348 B1 | 4/2002 | Canlas et al. |
| 6,387,113 B1 | 5/2002 | Hawkins et al. |
| 6,470,872 B1 | 10/2002 | Tiberius et al. |
| 6,493,217 B1 | 12/2002 | Jenkins, Jr. |
| 6,532,947 B1 | 3/2003 | Rosa et al. |
| 6,578,565 B2 | 6/2003 | Casas Salva |
| 6,613,011 B2 | 9/2003 | Castellano |
| 6,620,135 B1 | 9/2003 | Weston et al. |
| 6,766,795 B1 | 7/2004 | Sullivan |
| 6,786,379 B2 | 9/2004 | Largo |
| 6,851,447 B1 | 2/2005 | Carroll |
| 6,877,647 B2 | 4/2005 | Green et al. |
| 7,066,940 B2 | 6/2006 | Riedel et al. |
| 7,069,922 B1 | 7/2006 | Orr |
| 7,172,615 B2 | 2/2007 | Morriss et al. |
| 7,237,545 B2 | 7/2007 | Masse |
| 7,320,687 B2 | 1/2008 | Lee |
| 7,427,283 B2 | 9/2008 | Roger |
| 7,441,684 B2 | 10/2008 | Shelton, IV et al. |
| 7,445,619 B2 | 11/2008 | Auge, II et al. |
| 7,448,525 B2 | 11/2008 | Shelton, IV et al. |
| 7,455,655 B2 | 11/2008 | Alexandre et al. |
| 7,481,347 B2 | 1/2009 | Roy |
| 7,665,396 B1 | 2/2010 | Tippmann, Jr. |
| 7,765,999 B1 | 8/2010 | Stephens et al. |
| 8,052,691 B2 | 11/2011 | Zwirnmann et al. |
| 8,221,433 B2 | 7/2012 | Lozier |
| 2002/0165549 A1 | 11/2002 | Owusu-Akyaw et al. |
| 2002/0178901 A1 | 12/2002 | Bergstrom |
| 2003/0074021 A1 | 4/2003 | Morriss et al. |
| 2003/0195498 A1 | 10/2003 | Treat et al. |
| 2003/0225411 A1 | 12/2003 | Miller |
| 2004/0144012 A1 | 7/2004 | Adams |
| 2004/0158196 A1 | 8/2004 | Garitano et al. |
| 2004/0189258 A1 | 9/2004 | Lehmann et al. |
| 2005/0010168 A1 | 1/2005 | Kendall |
| 2005/0096661 A1 | 5/2005 | Farrow et al. |
| 2005/0119694 A1 | 6/2005 | Jacobs et al. |
| 2005/0131414 A1 | 6/2005 | Chana |
| 2005/0159752 A1 | 7/2005 | Walker et al. |
| 2005/0165394 A1 | 7/2005 | Boyce et al. |
| 2005/0188973 A1 | 9/2005 | Monks |
| 2005/0188977 A1 | 9/2005 | Wygant |
| 2006/0124118 A1 | 6/2006 | Dobbins |
| 2006/0217729 A1 | 9/2006 | Eskridge et al. |
| 2006/0241589 A1 | 10/2006 | Heim et al. |
| 2006/0293648 A1 | 12/2006 | Herzon |
| 2007/0017497 A1 | 1/2007 | Masse |
| 2007/0156175 A1 | 7/2007 | Weadock et al. |
| 2007/0169765 A1 | 7/2007 | Forster et al. |
| 2007/0175465 A1 | 8/2007 | Quinn et al. |
| 2007/0233133 A1 | 10/2007 | Cohen et al. |
| 2007/0235014 A1 | 10/2007 | Tiberius et al. |
| 2007/0270784 A1 | 11/2007 | Smith et al. |
| 2008/0015630 A1 | 1/2008 | Rousso |
| 2008/0029573 A1 | 2/2008 | Shelton et al. |
| 2008/0058820 A1 | 3/2008 | Harp |
| 2008/0103355 A1 | 5/2008 | Boyden et al. |
| 2008/0125784 A1 | 5/2008 | Rabiner et al. |
| 2008/0135598 A1 | 6/2008 | Burke et al. |
| 2008/0208251 A1 | 8/2008 | Weadock et al. |
| 2008/0221580 A1 | 9/2008 | Miller et al. |
| 2008/0228104 A1 | 9/2008 | Uber et al. |
| 2008/0251569 A1 | 10/2008 | Smith et al. |
| 2008/0255607 A1 | 10/2008 | Zemlok |
| 2008/0269754 A1 | 10/2008 | Lutz et al. |
| 2008/0272172 A1 | 11/2008 | Zemlok et al. |
| 2008/0281343 A1 | 11/2008 | Dewey et al. |
| 2008/0281353 A1 | 11/2008 | Aranyi et al. |
| 2008/0283570 A1 | 11/2008 | Boyden et al. |
| 2008/0283574 A1 | 11/2008 | Boyden et al. |
| 2008/0283577 A1 | 11/2008 | Boyden et al. |
| 2008/0294024 A1 | 11/2008 | Cosentino et al. |
| 2008/0296346 A1 | 12/2008 | Shelton, IV et al. |
| 2009/0018548 A1 | 1/2009 | Charles |
| 2009/0032003 A1 | 2/2009 | Masse |
| 2009/0032568 A1 | 2/2009 | Viola et al. |
| 2009/0082715 A1 | 3/2009 | Charles |
| 2009/0090763 A1 | 4/2009 | Zemlok et al. |
| 2009/0108048 A1 | 4/2009 | Zemlok et al. |
| 2009/0108049 A1 | 4/2009 | Roy |
| 2009/0112243 A1 | 4/2009 | Boyden et al. |
| 2009/0118738 A1 | 5/2009 | Gerondale |
| 2009/0131937 A1 | 5/2009 | Medoff |
| 2009/0163943 A1 | 6/2009 | Cavanaugh et al. |

(56) References Cited

U.S. PATENT DOCUMENTS

| | | |
|---|---|---|
| 2009/0171354 A1 | 7/2009 | Deville et al. |
| 2009/0206136 A1 | 8/2009 | Moore et al. |
| 2009/0209990 A1 | 8/2009 | Yates et al. |
| 2009/0235910 A1 | 9/2009 | Maeda |
| 2009/0240245 A1 | 9/2009 | Deville et al. |
| 2009/0241931 A1 | 10/2009 | Masse |
| 2009/0259220 A1 | 10/2009 | Appling et al. |
| 2009/0264893 A1 | 10/2009 | Beale et al. |
| 2009/0264940 A1 | 10/2009 | Beale et al. |
| 2009/0270834 A1 | 10/2009 | Nisato et al. |
| 2009/0299359 A1 | 12/2009 | Swain |
| 2010/0012698 A1 | 1/2010 | Liang et al. |
| 2010/0024791 A1 | 2/2010 | Romney |
| 2010/0030205 A1 | 2/2010 | Herzon |
| 2010/0036391 A1 | 2/2010 | Zaleski et al. |
| 2010/0069943 A1 | 3/2010 | Roe |
| 2010/0076455 A1 | 3/2010 | Birkenbach et al. |
| 2010/0126486 A1 | 5/2010 | Halmone et al. |
| 2010/0154767 A1 | 6/2010 | Masse |
| 2010/0305624 A1 | 12/2010 | Lozier et al. |

FOREIGN PATENT DOCUMENTS

| | | |
|---|---|---|
| EP | 1859749 A2 | 11/2007 |
| WO | WO-9522934 A1 | 8/1995 |
| WO | WO-2010138538 A1 | 12/2010 |

OTHER PUBLICATIONS

"European Application Serial No. 10727219.7, Office Action mailed Feb. 3, 2012", 2 pgs.

"European Application Serial No. 10727219.7, Office Action mailed Mar. 26, 2012", 1 pg.

"European Application Serial No. 10727219.7, Response filed Aug. 10, 2012 to Office Action mailed Feb. 3, 2012", 12 pgs.

"Polysorb™ Meniscal Stapler XLS Device", [Online]. Retrieved from the Internet: <URL: http://www.sportssurgery.com/sportsmedicine/pageBuilder.aspx?topicID=31604>, (2008), 1 pg.

"The Staple (Biomet's Meniscal Stapler CO2 Gun)", [Online]. Retrieved from the Internet: <URL: http://www.biomet.com/sportsmedicine/getFile.cfm?id=1055&rt=inline>, (1999), 2 pgs.

"U.S. Appl. No. 12/787,518, Notice of Allowance mailed Apr. 26, 2012", 12 pgs.

"U.S. Appl. No. 12/787,518, Response filed Jan. 30, 2012 to Restriction Requirement mailed Jan. 3, 2012", 2 pgs.

"U.S. Appl. No. 12/787,518, Restriction Requirement mailed Jan. 3, 2012", 6 pgs.

"International Application Serial No. PCT/US2010/036126, International Preliminary Report on Patentability mailed Nov. 29, 2011", 5 pgs.

"International Application Serial No. PCT/US2010/036126, International Preliminary Report on Patentability mailed Dec. 8, 2011", 6 pgs.

"International Application Serial No. PCT/US2010/036126, International Search Report and Written Opinion dated Sep. 13, 2010", 10 pgs.

"International Application Serial No. PCT/US2010/036126, International Search Report mailed Sep. 22, 2010", 3 pgs.

"International Application Serial No. PCT/US2010/036126, Written Opinion mailed Sep. 22, 2010", 4 pgs.

"Repairing Fractured Bones by Use of Bioabsorbable Composites", Langley Research Center, Tech Briefs, [Online]. Retrieved from the Internet: <http://www.techbriefs.com/component/content/5/5?task=view>., (Sep. 2, 2006), 2 pgs.

* cited by examiner

BONE FIXATION TOOL

CROSS REFERENCE TO RELATED APPLICATIONS

This patent application is a continuation of U.S. patent application Ser. No. 12/787,518, entitled "BONE FIXATION TOOL," filed May 26, 2010, which claims priority from U.S. Provisional Patent Application Ser. No. 61/181,024, entitled "BONE FIXATION," filed May 26, 2009, the disclosure of which are hereby expressly incorporated each by reference herein in its entirety.

BACKGROUND

1. Field of the Disclosure.

The present disclosure relates to a tool and a method for driving a bone pin into a fractured bone to stabilize the fractured bone. More particularly, the present disclosure relates to a tool and a method for driving a bone pin into a fractured bone to stabilize the fractured bone by maintaining the fractured bone in a reduced state.

2. Description of the Related Art.

Complex or comminuted bone fractures produce multiple bone fragments. In operation, these fragments may be reduced and temporarily secured together prior to more permanently fixing the fragments together, such as with external plating.

Current devices for reducing and temporarily securing together bone fragments possess several disadvantages. External fixation devices, such as clamps, are bulky and may require invasive surgical procedures. Also, internal fixation devices, such as metallic pins and guide wires, may be difficult to drive into the bone fragments and may extend externally from the fragments while interfering with external plating.

SUMMARY

The present disclosure relates to a tool and a method for driving a bone pin into a fractured bone to stabilize the fractured bone by maintaining the fractured bone in a reduced state. In certain embodiments, the bone pin may be used to temporarily stabilize the fractured bone prior to more permanent fixation. The tool may be a handheld device including a cartridge having at least one passageway that receives the bone pin. The tool may also include a pneumatically-powered piston having a needle that is sized for receipt within the passageway of the cartridge, the needle applying sufficient force to the bone pin to drive the bone pin out of the cartridge and into the fractured bone.

According to an embodiment of the present disclosure, a handheld tool is provided for stabilizing a fractured bone, the handheld tool having a proximal end and a distal end. The handheld tool includes: a housing; at least one bone pin configured to be driven into the fractured bone to stabilize the fractured bone; a cartridge supported by the housing and including at least one passageway that receives the bone pin, the passageway sized to accommodate axial movement of the bone pin through the passageway while limiting radial movement of the bone pin in the passageway; and a piston that translates axially relative to the housing, the piston including a head arranged toward the proximal end of the handheld tool and a needle arranged toward the distal end of the handheld tool, the needle sized for receipt within the passageway of the cartridge, the needle applying sufficient force to the bone pin to drive the bone pin axially from the cartridge and into the fractured bone.

According to another embodiment of the present disclosure, a handheld tool is provided for stabilizing a fractured bone, the handheld tool having a proximal end and a distal end. The handheld tool includes a housing; at least one bone pin configured to be driven into the fractured bone to stabilize the fractured bone; a cartridge supported by the housing at the distal end of the handheld tool, the cartridge including at least one passageway that receives the bone pin; and a piston that translates axially relative to the housing, the piston including a head arranged toward the proximal end of the handheld tool and a needle arranged toward the distal end of the handheld tool, the needle sized for receipt within the passageway of the cartridge, the needle applying sufficient force to the bone pin to drive the bone pin axially from the cartridge and into the fractured bone.

According to yet another embodiment of the present disclosure, a handheld tool is provided for driving a bone pin into a fractured bone to stabilize the fractured bone, the handheld tool having a proximal end and a distal end. The handheld tool includes: a housing; a cartridge supported by the housing and including at least one passageway that is sized to receive the bone pin; a piston that translates axially relative to the housing, the piston including a head arranged toward the proximal end of the handheld tool and a needle arranged toward the distal end of the handheld tool, the needle sized for receipt within the passageway of the cartridge, the needle applying sufficient force to the bone pin to drive the bone pin axially from the cartridge and into the fractured bone; a pressurized gas source coupled to the housing for supplying a pneumatic force to the head of the piston to axially translate the piston relative to the housing; a valve assembly having a normally closed state to close a flow of pressurized gas from the pressurized gas source to the head of the piston and an open state to open the flow of pressurized gas from the pressurized gas source to the head of the piston; and a trigger assembly coupled to the valve assembly to adjust the valve assembly from the normally closed state to the open state, the valve assembly automatically returning to the normally closed state following the open state.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

The present disclosure provides a tool and method for reducing and securing together bone fragments, which may serve as a temporary solution prior to more permanent fixation of the bone fragments. According to an exemplary embodiment of the present disclosure, a biocompatible polymer may be inserted into the bone fragments to secure the bone fragments together. The polymer may remain in the patient's body over time, or the polymer may absorb into the patient's body.

In one embodiment, the polymer may be injected into the bone fragments in a liquid or semi-liquid state and then cured to secure the bone fragments together. Such polymers may cure upon contact with light or water, for example. A suitable polymer that may be injected into the bone fragments includes a quick-setting cyanoacrylate (commonly sold under trade names like Super Glue® and Krazy Glue®). It is within the scope of the present disclosure that the polymer may be blended with other materials for injection into the bone fragments, such as elastic, thread-like fibers.

In another embodiment, the polymer may be driven into the bone fragments in a solid state to secure the bone fragments together. Suitable polymers that may be driven into the bone fragments include biodegradable polymers, such as polylactide (PLA).

Figure 1A:
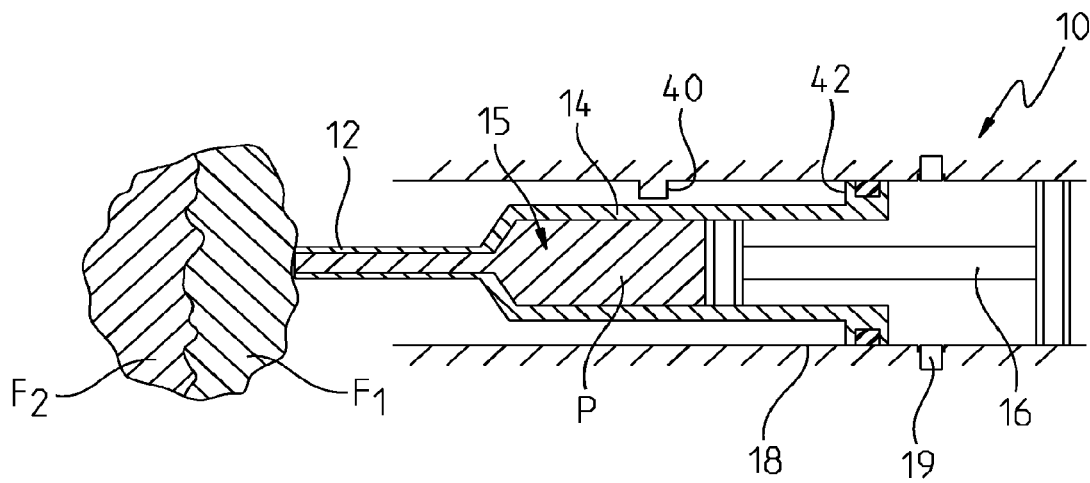
FIG. 1A is a schematic diagram representing an exemplary tool of the present disclosure, showing a needle of the tool aligned with a first bone fragment and a second bone fragment.
Figure 1B:
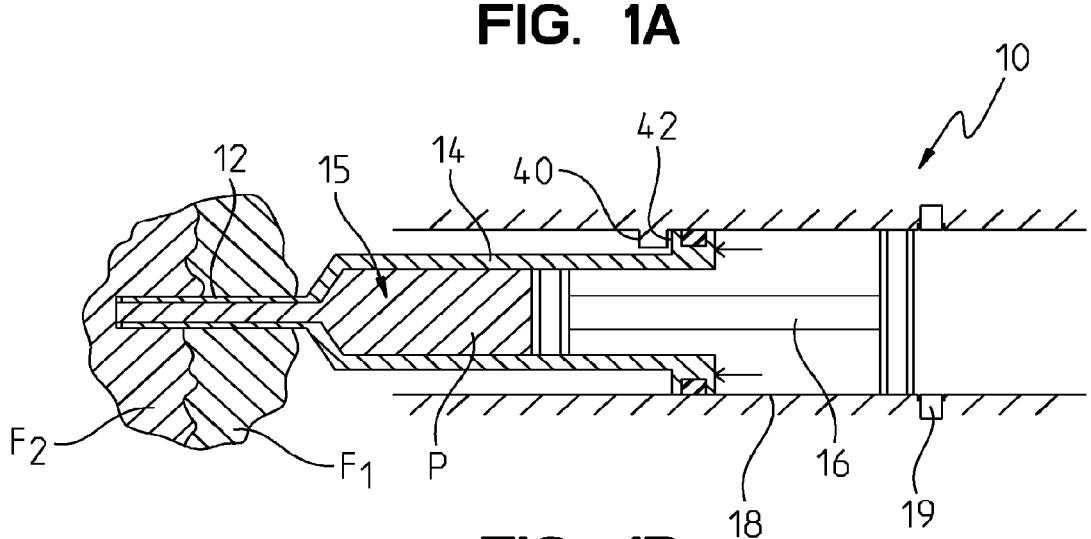
FIG. 1B is a schematic diagram of the tool of FIG. 1A, showing the needle of the tool inserted through the first bone fragment and into the second bone fragment.
Figure 1C:
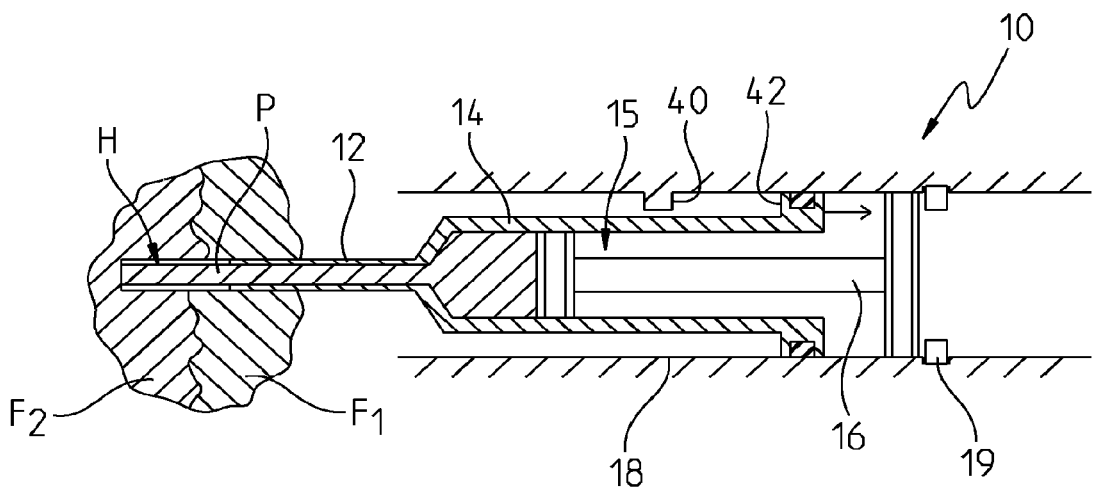
FIG. 1C is a schematic diagram of the tool of FIG. 1B, showing the needle of the tool being withdrawn to expose a hole in the bone fragments and showing a biocompatible polymer material being injected into the hole.

Referring initially to FIGS. 1A-1C, an exemplary method for reducing and securing together bone fragments is illustrated schematically. Tool 10, which is similar in construction to a syringe, is provided for performing this method and includes needle 12, tube or cylinder 14 defining chamber 15 therein, plunger 16, and housing 18.

In a first step of the illustrative method, and as shown in FIG. 1A, first bone fragment $F_1$ is aligned with an adjacent, second bone fragment $F_2$. Tool 10 is placed near or in contact with first bone fragment $F_1$.

Next, as shown in FIG. 1B, sufficient force is applied to cylinder 14 of tool 10 to drive needle 12 through first bone fragment $F_1$ and into second bone fragment $F_2$. Tool 10 may be provided with needles 12 of various sizes to accommodate different fractures and bone types. For example, needles 12 may be provided in lengths of approximately 0.25 inch, 0.5 inch, 1.0 inch, 1.5 inches, 2.0 inches, or more. Also, needles 12 may be provided in diameters of approximately 1 millimeter (mm), 1.5 mm, 2 mm, 2.5 mm, 3 mm, or more, for example.

Finally, as shown in FIG. 1C, needle 12 of tool 10 is pulled out of bone fragments $F_1$, $F_2$, to expose hole H in bone fragments $F_1$, $F_2$. As needle 12 retracts from bone fragments $F_1$, $F_2$, pressure may be applied to plunger 16 to deliver a biocompatible polymer material P from chamber 15 of cylinder 14 into hole H. According to an exemplary embodiment of the present method, a biocompatible polymer material P includes fluid cyanoacrylate containing a bundle of thread-like fibers. The internal walls of cylinder 14 lining chamber 15 may include a non-stick coating, such as polytetrafluoroethylene (PTFE), to prevent polymer material P from drying thereon. Also, chamber 15 of cylinder 14 may contain at least enough polymer material P to adequately fill hole H. Over time, such as less than a few minutes, the biocompatible polymer material P cures or hardens in hole H to bind bone fragments $F_1$, $F_2$, together.

Figure 1D:
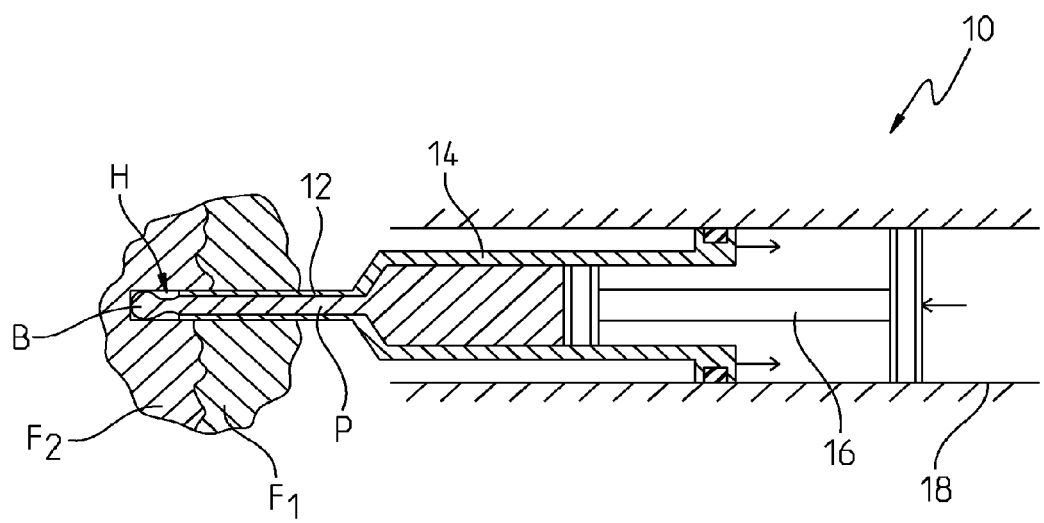
FIG. 1D is a schematic diagram similar to FIG. 1C, showing the needle of the tool withdrawn to expose a hole in the bone fragments and showing a biocompatible polymer material injected into the hole to form a bulbous fiber portion.

According to an exemplary embodiment of the present method, bursts of polymer material P may be delivered into hole H to form bulbous fiber portions B in hole H, as shown in FIG. 1D. These bulbous fiber portions B may serve as anchors, preventing the polymer from loosening in hole H. To form bulbous fiber portions B, the initial removal of needle 12 from hole H may be slowed or delayed while plunger 16 is activated to deliver an initial burst of polymer material P. Then, needle 12 may be retracted to deliver an even, thread-like stream of polymer material P extending out of hole H.

Figure 1E:
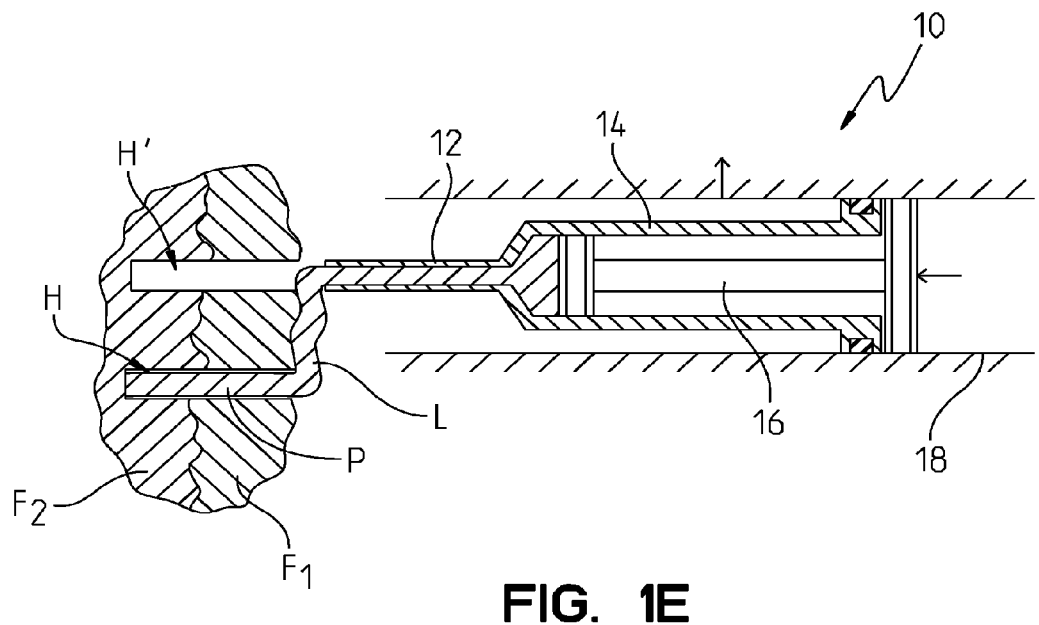
FIG. 1E is a schematic diagram of the tool of FIG. 1C, showing a biocompatible polymer material being injected into an adjacent hole to form a loop.

According to another exemplary embodiment of the present method, and as shown in FIG. 1E, after delivering the biocompatible polymer material P into hole H, tool 10 may be moved to a different location on first bone fragment $F_1$, such as adjacent to second hole H' in first bone fragment $F_1$. Hole H' may be formed by needle 12 or by another needle. As shown in FIG. 1E, the biocompatible polymer material P may continue being dispensed from tool 10 during this movement from hole H to hole H', thereby forming a continuous loop L of polymer material P that extends across the surface of first bone fragment $F_1$ and connects adjacent filled holes H, H', similar to the behavior of a sewing machine. Stitching together the polymer material P in adjacent holes H, H', may stabilize the connection between bone fragments $F_1$, $F_2$.

Tool 10 may be powered pneumatically, hydraulically, electrically (e.g. with batteries), and/or electromagnetically. For example, tool 10 may behave similar to a compressed air nail gun. When a trigger (not shown) of tool 10 is pulled, compressed air may be released to force cylinder 14 and needle 12 coupled thereto forward inside housing 18 until needle 12 projects beyond housing 18, through first bone fragment $F_1$, and into second bone fragment $F_2$, as shown in FIG. 1B. When the trigger of tool 10 is released, needle 12 and cylinder 14 may retract back into housing 18, leaving behind hole H in bone fragments $F_1$, $F_2$, as shown in FIG. 1C. Needle 12 and cylinder 14 of tool 10 may be biased in this retracted position of FIG. 1C relative to housing 18 by any suitable mechanism, including, for example, a spring or a magnet.

To deliver the biocompatible polymer material P into hole H, tool 10 may be provided with a suitable catch mechanism for blocking retraction of plunger 16. The catch mechanism may include latch 19, as shown in FIG. 1C, or a magnet, for example. When the trigger (not shown) of tool 10 is pulled to move needle 12 and cylinder 14 forward within housing 18, as shown in FIGS. 1A-1B, latch 19 may be in an unlocked position, allowing plunger 16 to travel forward along with needle 12. When the trigger of tool 10 is released to retract needle 12 and cylinder 14 back into housing 18, as shown in FIG. 1C, latch 19 may move to a locked position to engage plunger 16. The sliding cylinder 14 will travel over the stationary plunger 16 that is being held in place by latch 19, forcing the biocompatible polymer material P contained inside chamber 15 of cylinder 14 to be dispensed from needle 12. After a sufficient amount of biocompatible polymer material P is delivered from needle 12, latch 19 may be released, allowing plunger 16 to retract into housing 18 relative to cylinder 14.

Tool 10 may be capable of controlling the depth that needle 12 travels into bone fragments $F_1$, $F_2$ (FIGS. 1A-1C). According to an exemplary embodiment of the present disclosure, the depth of needle 12 in bone fragments $F_1$, $F_2$, is controlled by limiting the distance that needle 12 projects from housing 18. For example, as shown in FIG. 1B, housing 18 includes at least one stop 40 that cooperates with flange 42 of cylinder 14 to limit the forward travel of needle 12 out of housing 18 and toward bone fragments $F_1$, $F_2$.

Figure 2A:
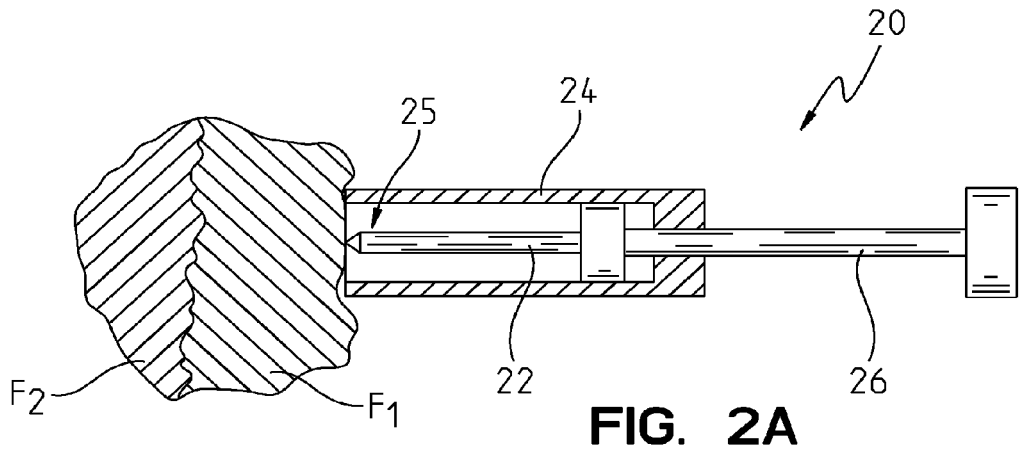
FIG. 2A is a schematic diagram representing another tool of the present disclosure, showing the tool aligned with a first bone fragment and a second bone fragment.
Figure 2B:
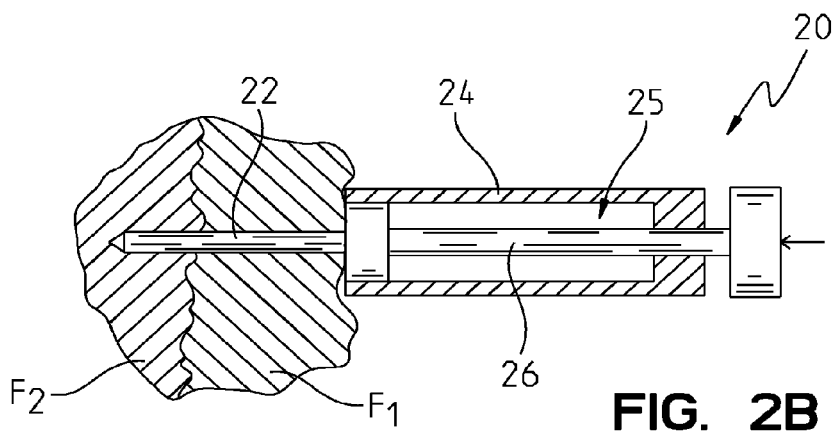
FIG. 2B is a schematic diagram of the tool of FIG. 2A, showing the tool driving a polymeric rod through the first bone fragment and into the second bone fragment.
Figure 2C:
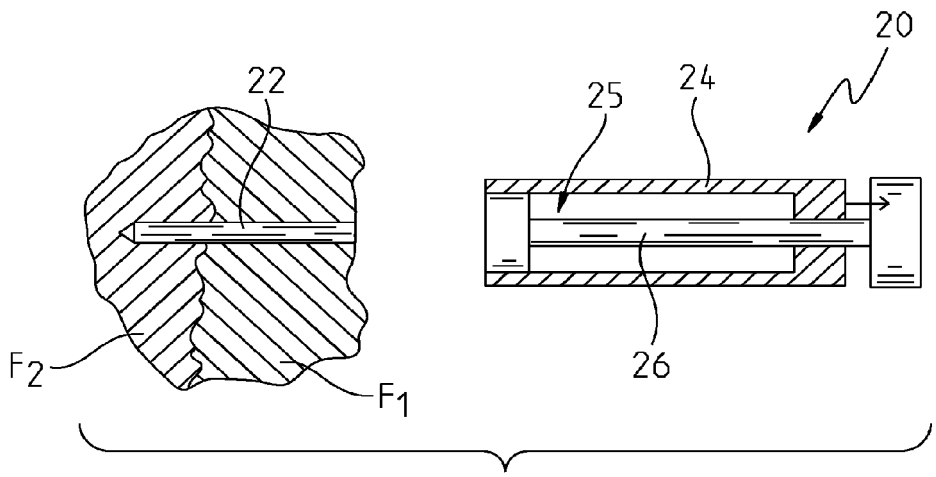
FIG. 2C is a schematic diagram of the tool of FIG. 2B, showing the tool removed from the bone fragments while leaving behind the polymeric rod to secure the bone fragments together.

Referring next to FIGS. 2A-2C, another exemplary method for reducing and securing together bone fragments is illustrated schematically. Tool 20, which is similar in construction to a syringe, is provided for performing this method and includes polymeric needle or rod 22, tube or cylinder 24 defining chamber 25 therein, and plunger 26.

In a first step of the illustrative method, and as shown in FIG. 2A, first bone fragment $F_1$ is aligned with an adjacent, second bone fragment $F_2$. Tool 20 is placed near or in contact with first bone fragment $F_1$.

Next, as shown in FIG. 2B, sufficient force is applied to plunger 26 of tool 20 to drive rod 22 through the first bone fragment $F_1$ and into the second bone fragment $F_2$. According to an exemplary embodiment of the present method, rod 22 is constructed of a rigid polymer, such as polylactide (PLA), polystyrene, poly methyl methacrylate, polycarbonate, or a fiber-reinforced polymer, for example. According to another exemplary embodiment of the present method, rod 22 is constructed of a biocompatible, non-ferrous metal, such as magnesium.

Finally, as shown in FIG. 2C, tool 20 is pulled away from bone fragments $F_1$, $F_2$, leaving polymeric rod 22 behind within bone fragments $F_1$, $F_2$, to bind bone fragments $F_1$, $F_2$, together. According to an exemplary embodiment of the present method, rod 22 has a textured outer surface to resist loosening or pull-out from bone fragments $F_1$, $F_2$. Rod 22 need not be attached to plunger 26, so that, when tool 20 is pulled away from bone fragments $F_1$, $F_2$, rod 22 is left behind. The illustrated chamber 25 of cylinder 24 may be exaggerated in size relative to polymeric rod 22. For example, cylinder 24 may be sized such that polymeric rod 22 is radially constrained by cylinder 24, while being permitted to slide axially within chamber 25 of cylinder 24.

As shown in FIGS. 2A-2C, polymeric rod 22 is provided in a suitable length to extend into bone fragment $F_2$ and end substantially flush with bone fragment $F_1$. It is also within the scope of the present disclosure that rod 22 may have excess length that may be trimmed before or after rod 22 is implanted so that rod 22 ends substantially flush with bone fragment $F_1$. For example, before pulling tool 20 away from bone fragments $F_1$, $F_2$, rod 22 may be trimmed along the bone-facing end of cylinder 24 to remove any excess length from rod 22. As another example, after pulling tool 20 away from bone fragments $F_1$, $F_2$, rod 22 may be trimmed along bone fragment $F_1$ to remove any excess length from rod 22.

Tool 20 may be powered pneumatically, hydraulically, electrically (e.g. with batteries), and/or electromagnetically. For example, tool 20 may behave similar to a compressed air nail gun. When a trigger (not shown) of tool 20 is pulled, compressed air may be released to force plunger 26 forward inside cylinder 24 until rod 22 projects beyond cylinder 24, through first bone fragment $F_1$, and into second bone fragment $F_2$, as shown in FIG. 2B. When the trigger of tool 20 is released, plunger 26 may retract back into cylinder 24, leaving behind rod 22 in bone fragments $F_1$, $F_2$. Plunger 26 of tool 20 may be biased in this retracted position relative to cylinder 24 by any suitable mechanism, including, for example, a spring or a magnet.

In addition to securing together bone fragments, the methods described above may also be used to secure together soft tissue of the body. The methods described above may also be used to mount orthopedic components onto bone, including cut guides, bone plates, and/or cerclage wires.

Figure 3:
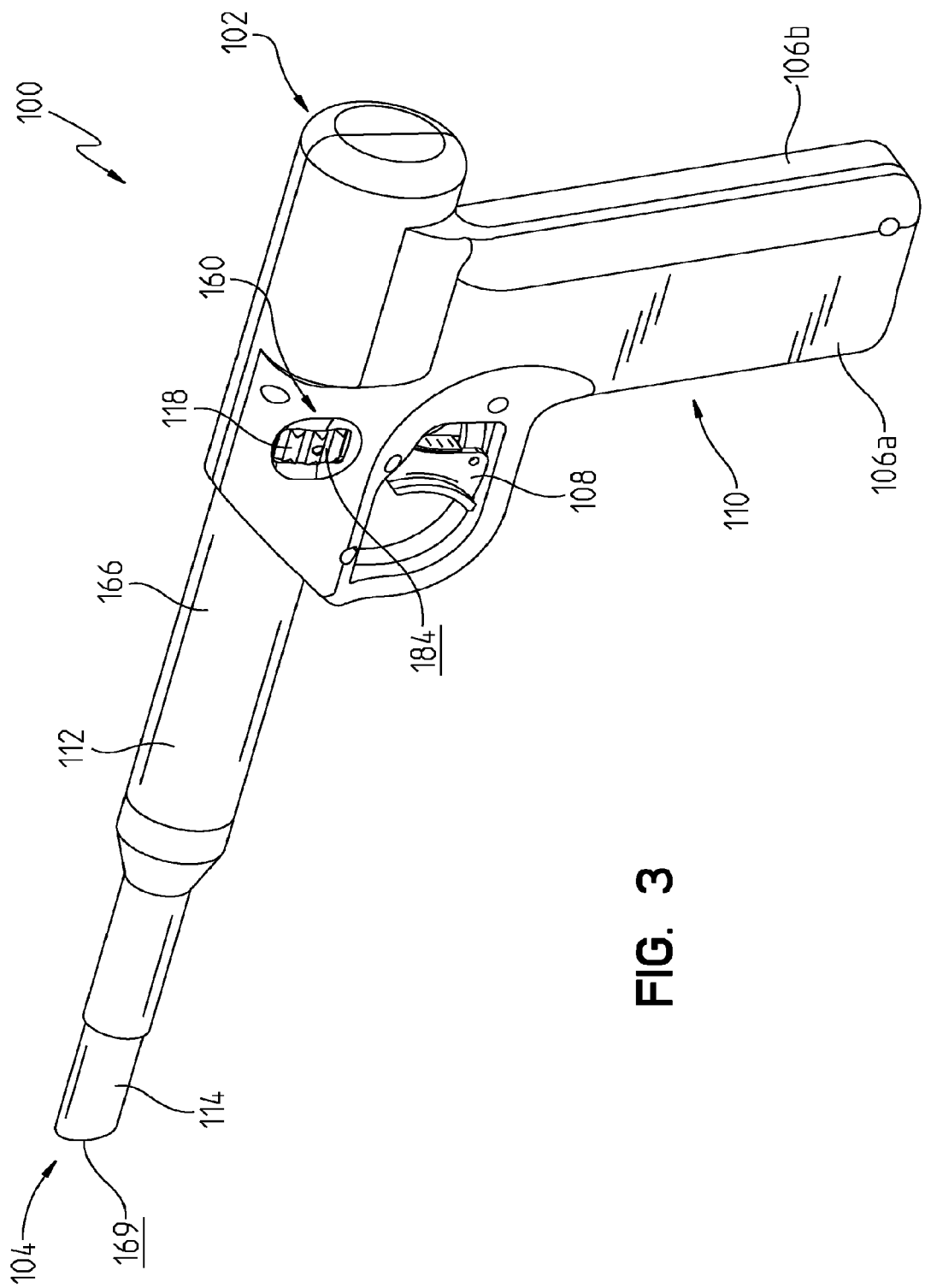
FIG. 3 is a perspective view of an exemplary tool of the present disclosure.

Referring next to FIGS. 3-12, an exemplary handheld pneumatic tool 100 is provided for reducing and securing together bone fragments. Tool 100 extends between a first, proximal end 102 and a second, distal end 104. As shown in FIG. 3, proximal end 102 of tool 100 includes left-side housing 106a, right-side housing 106b, and trigger 108. Left-side housing 106a and right-side housing 106b of tool 100 cooperate to define handle 110. Distal end 104 of tool 100 includes barrel 112 and nose 114. In operation, with distal end 104 of tool 100 positioned against a fractured bone, a surgeon may grip handle 110 and pull trigger 108.

Figure 4:
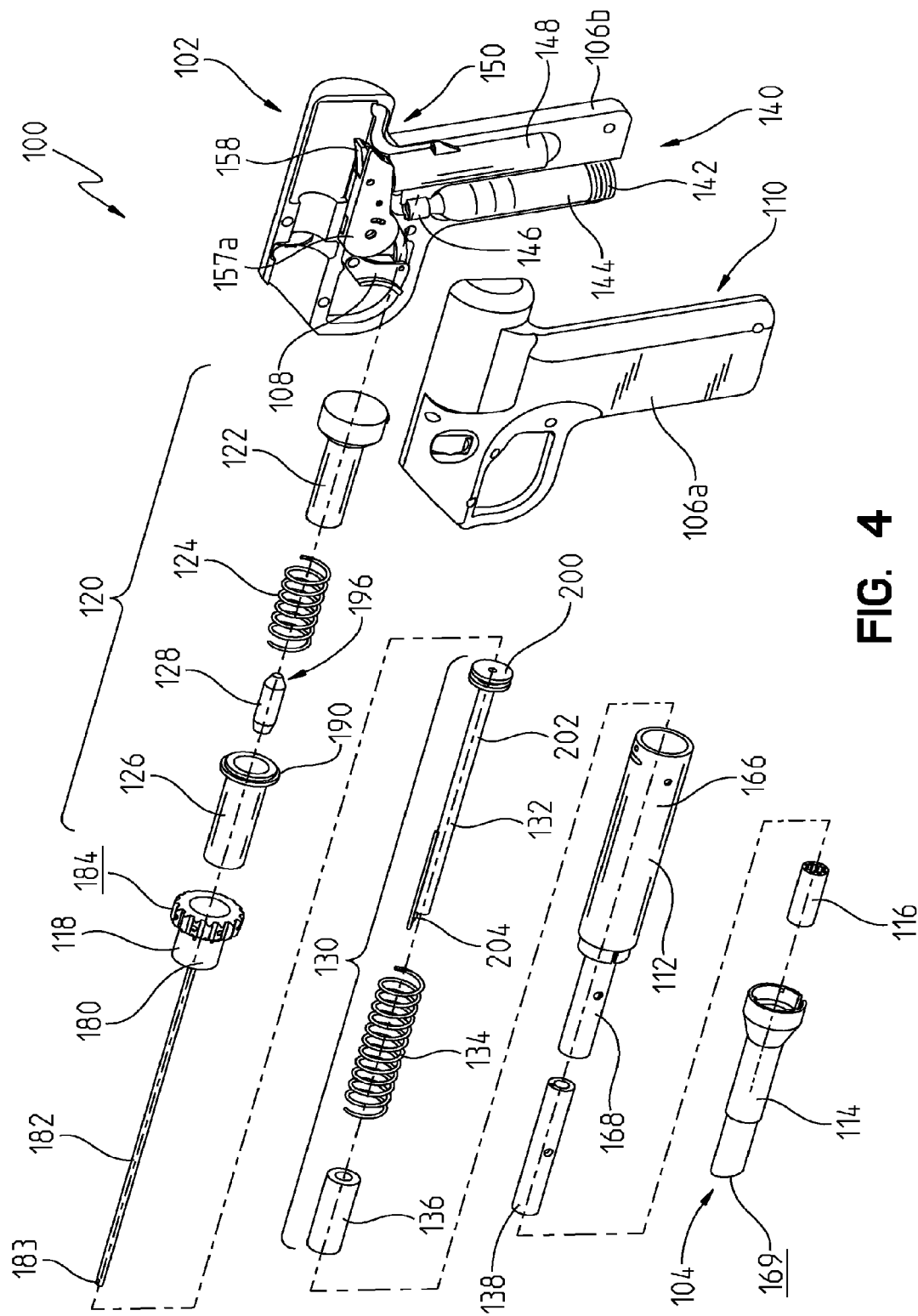
FIG. 4 is an exploded perspective view of the tool of FIG. 3 showing a valve assembly and a piston assembly.

With reference to FIG. 4, tool 100 also includes cartridge 116, dial 118, valve assembly 120, and piston assembly 130. Valve assembly 120 of tool 100 includes valve body 122, valve return spring 124, plug bolt 126, and plug 128. Piston assembly 130 of tool includes piston 132, piston return spring 134, damper 136, and guide 138. Each component of FIG. 4 is described further below.

Figure 6:
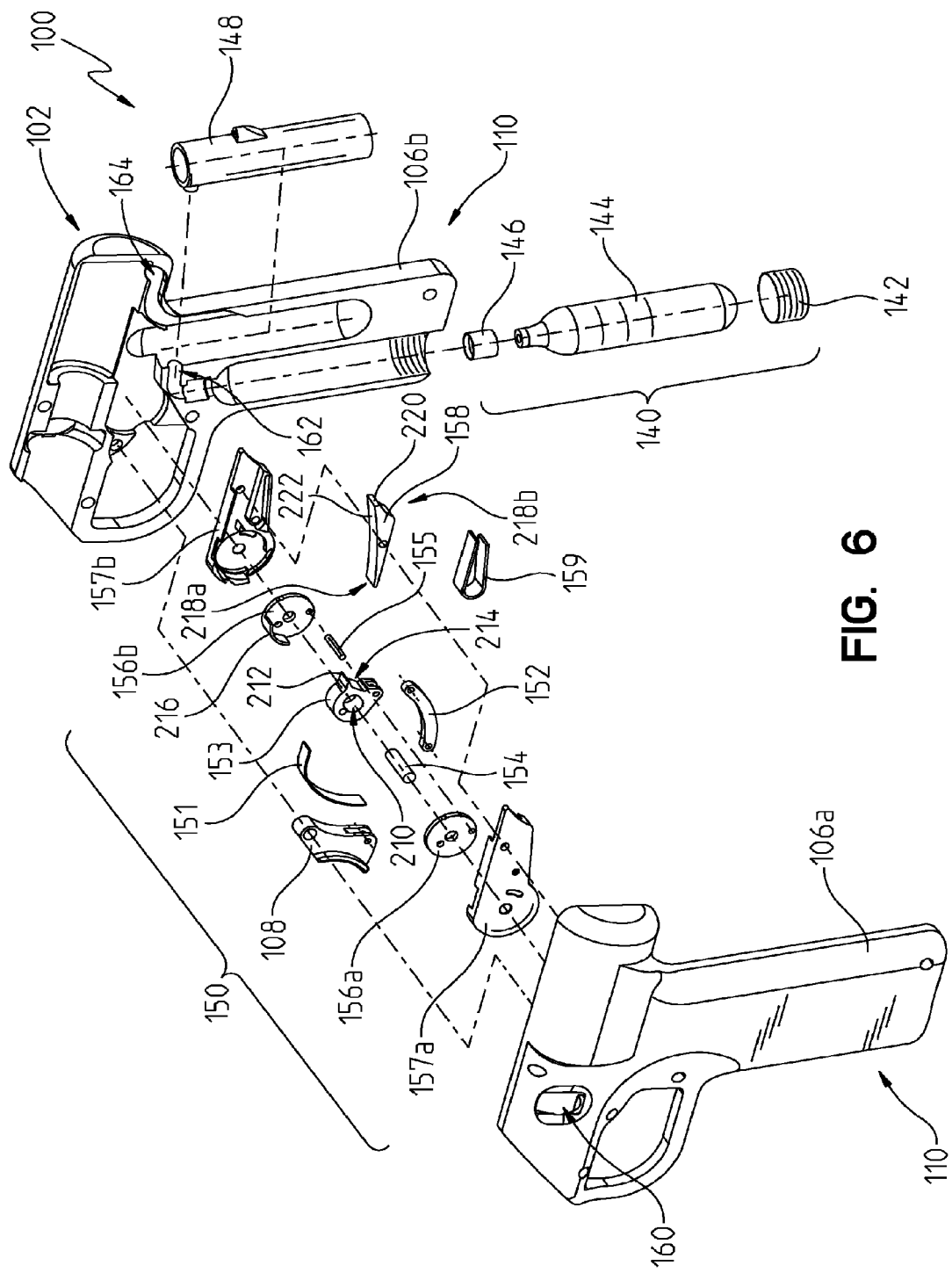
FIG. 6 is another exploded perspective view of the tool of FIG. 3 showing a trigger assembly and a gas supply assembly.

With reference to FIG. 6, tool 100 further includes gas supply assembly 140 and trigger assembly 150. Gas supply assembly 140 of tool 100 includes cap 142, gas canister 144, puncture valve 146, and regulator 148. Trigger assembly 150 of tool 100 includes trigger 108, trigger spring 151, an arcuate linkage 152, rotating pawl 153, shaft 154, stop pin 155, left-side casing 156a, right-side casing 156b, left-side holder 157a, right-side holder 157b, a lock or seer 158, and a U-shaped seer spring 159. Each component of FIG. 6 is described further below.

Left-side housing 106a and right-side housing 106b of tool 100 cooperate to conceal and support valve assembly 120, gas supply assembly 140, and trigger assembly 150 of tool 100. As shown in FIG. 3, housing 106a defines external opening 160 so that dial 118 may be accessible through housing 106a. Housings 106a, 106b, cooperate to define first gas channel 162 that connects gas canister 144 to regulator 148 and second gas channel 164 that connects regulator 148 to valve body 122, as shown in FIG. 6. In operation, pressurized gas travels from gas canister 144 to regulator 148 via first gas channel 162 of housings 106a, 106b, and from regulator 148 to valve body 122 via second gas channel 164 of housings 106a, 106b.

Barrel 112 of tool 100 is a hollow component that extends from housings 106a, 106b, as shown in FIG. 3. Barrel 112 includes proximal portion 166 situated toward proximal end 102 of tool 100 and distal portion 168 situated toward distal end 104 of tool 100. Barrel 112 is sized to receive piston assembly 130 therein. More particularly, proximal portion 166 of barrel 112 is sized to receive piston return spring 134 and damper 136 of piston assembly 130 therein, and distal portion 168 of barrel 112 is sized to receive guide 138 of piston assembly 130 therein, with piston 132 of piston assembly 130 extending along substantially the entire length of barrel 112 between both proximal portion 166 and distal portion 168 of barrel 112. As shown in FIG. 4, proximal portion 166 of barrel 112 may be larger in diameter than distal portion 168 of barrel 112 to accommodate piston 132, piston return spring 134, and damper 136 of piston assembly 130.

Nose 114 of tool 100 is a hollow component that extends from barrel 112 to define distal end 104 of tool 100, as shown in FIG. 3. Nose 116 includes bone-contacting surface 169 that is configured to rest against the patient's bone. Bone-contacting surface 169 of nose 116 may be textured (e.g. toothed, spiked) to gain purchase on the patient's bone without slippage. Nose 114 is sized to receive cartridge 116 therein. Also, nose 114 may be sized to receive at least a portion of barrel 112 therein, including the narrow, distal portion 168 of barrel 112.

Figure 5:
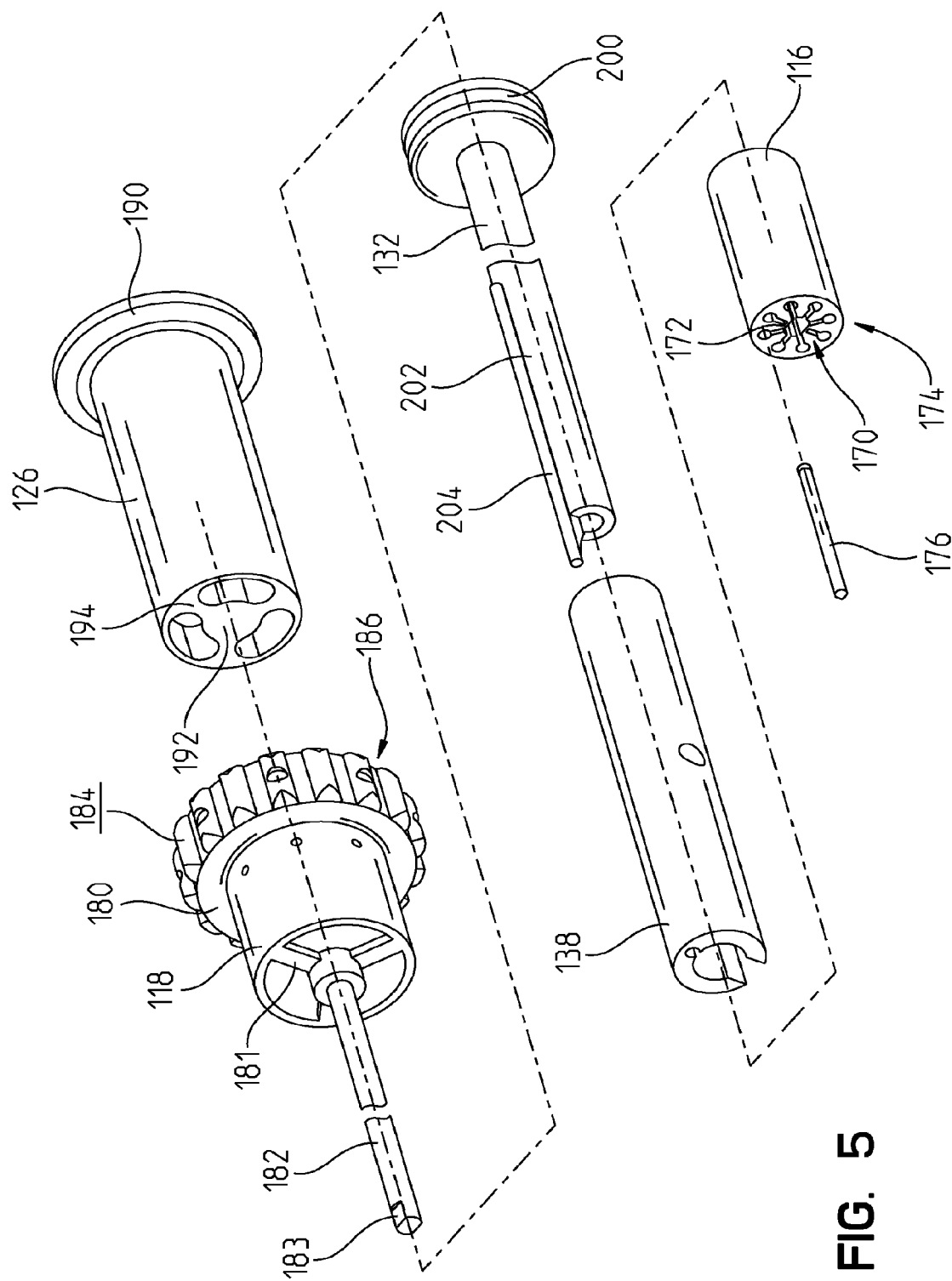
FIG. 5 is an exploded perspective view of selected components of the valve assembly and the piston assembly of FIG. 4.

Cartridge 116 of tool 100 is a cannulated component that is sized for receipt within nose 114 of tool 100, such that cartridge 116 may be positioned at distal end 104 of tool 100. As shown in FIG. 5, cartridge 116 includes cannula 170 that is bordered by at least one flat 172. Around cannula 170, cartridge 116 further includes a plurality of elongate slots or passageways 174. Each passageway 174 of cartridge 116 is sized to receive a biocompatible rod or pin 176 therein. Each passageway 174 may be distinct, or, as shown in FIG. 5, multiple passageways 174 may be interconnected. According to an exemplary embodiment of the present disclosure, passageways 174 of cartridge 116 are sized to limit each pin 176 to axial movement through the corresponding passageway 174, thereby stabilizing pins 176 and ensuring that pins 176 are delivered along a straight path to avoid bending and/or breaking After use, cartridge 116 may be removed from tool 100 and either refilled with new pins 176 or replaced.

Pin 176 is configured to be driven into bone fragments to secure the bone fragments together. Pin 176 may be constructed of a biocompatible polymer, and in certain embodiments, the biocompatible polymer may be biodegradable. For example, pin 176 may be constructed of a biodegradable polymer, such as polylactide (PLA). Pin 176 may also be constructed of polystyrene, poly methyl methacrylate, polycarbonate, or a fiber-reinforced polymer, for example. It also is within the scope of the present disclosure that pin 176 may be constructed of a biocompatible, non-ferrous metal, such as magnesium. Each pin 176 may have a length as small as approximately 0.5 inch, 0.6 inch, 0.7 inch, 0.8 inch, 0.9 inch, or less, and as large as approximately 1.0 inch, 1.1 inches, 1.2 inches, 1.3 inches, 1.4 inches, 1.5 inches, or more. Each pin 176 may have a diameter as small as approximately 0.03 inch, 0.04 inch, 0.05 inch, or 0.06 inch, and as large as approximately 0.07 inch, 0.08 inch, 0.09 inch, 0.10 inch, or more. Depending on the size of pin 176 and the material used to construct pin 176, the weight of pin 176 may be less than about 0.01 gram, such as approximately 0.005 gram, 0.006 gram, or 0.007 gram. An exemplary pin 176 may not impede subsequent fixation. For example, pin 176 may be sufficiently small in size and/or low in density that the surgeon may drill through pin 176 during a subsequent procedure.

Dial 118 of tool 100 includes a generally hollow head 180 that is sized for receipt within housings 106a, 106b, and shaft 182 that extends axially through barrel 112 and into nose 114, as shown in FIG. 4. A plurality of spaced apart rims 181 join head 180 to shaft 182, as shown in FIG. 5, to accommodate airflow through head 180 and around shaft 182 of dial 118.

Dial 118 couples to cartridge 116 for rotation therewith. For example, as shown in FIG. 5, shaft 182 of dial 118 extends through cannula 170 of cartridge 116 and includes at least one flat 183 that mates with flat 172 of cartridge 116 to transfer rotational movement of dial 118 to cartridge 116. Head 180 of dial 118 may include a textured or knurled exterior surface 184 to facilitate the turning of dial 118. As shown in FIG. 3, knurled exterior surface 184 of dial 118 is exposed through external opening 160 in housing 106a so that the surgeon may access and turn dial 118.

Dial 118 may include a suitable detent mechanism to ensure proper alignment of cartridge 116. For example, as shown in FIG. 5, head 180 of dial 118 includes a plurality of evenly spaced alignment holes 186 therein. Each alignment hole 186 may be sized to receive a ball 187 (FIG. 8) or another suitable detent to ensure that dial 118, and cartridge 116 coupled thereto, are rotated to one of a discrete number of positions.

Figure 7:
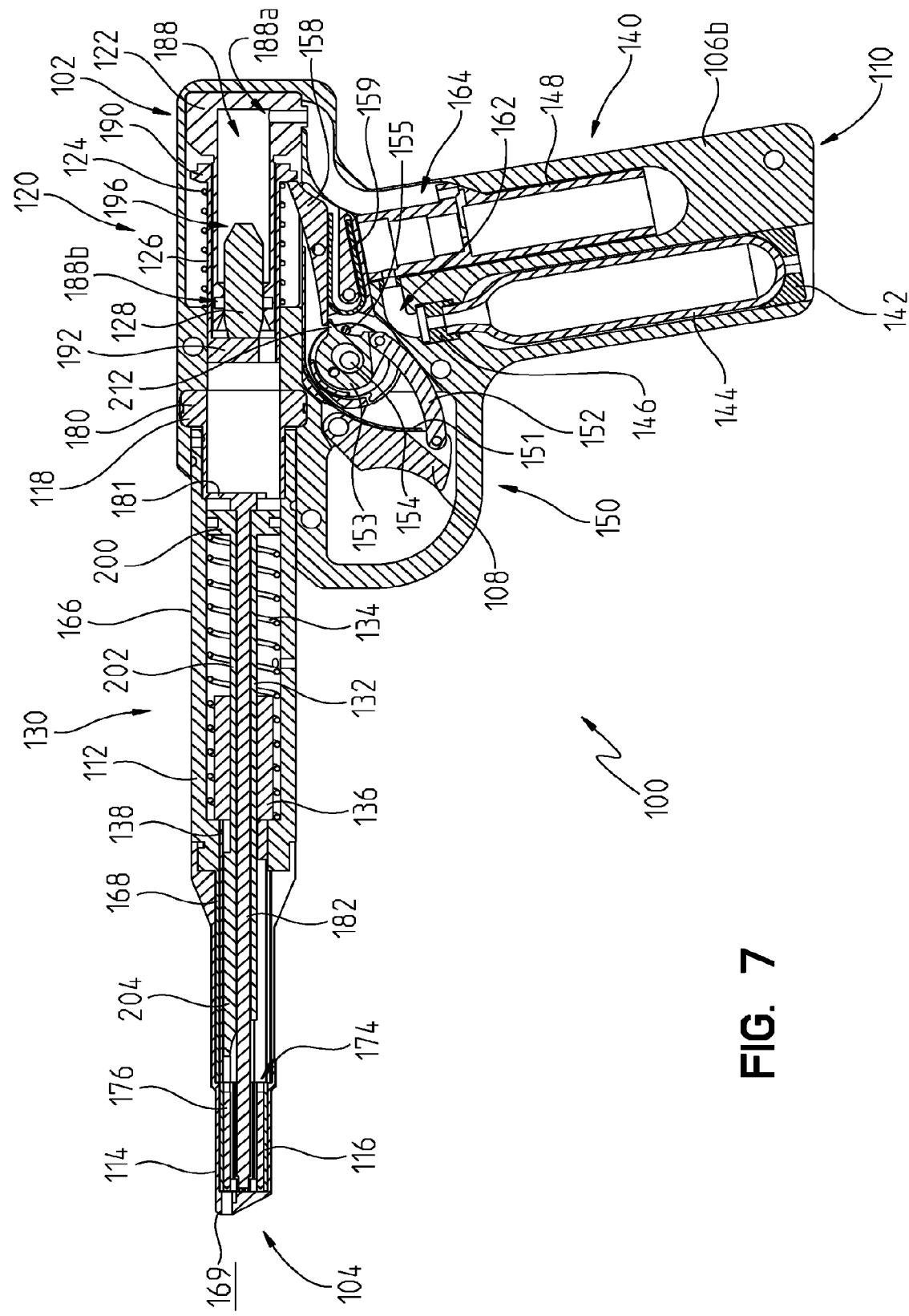
FIG. 7 is a cross-sectional view of the tool of FIG. 3 shown at rest before being fired.

Valve assembly 120 of tool 100 is received within housings 106a, 106b, and includes valve body 122, valve return spring 124, plug bolt 126, and plug 128. As shown in FIG. 7, valve body 122 is a generally hollow component that defines gas chamber 188 therein. Gas chamber 188 of valve body 122 includes inlet 188a that communicates with second gas channel 164 of housings 106a, 106b, to receive pressurized gas from gas supply assembly 140. Gas chamber 188 of valve body 122 also includes a sealed, chamfered outlet 188b that communicates with piston assembly 130 to deliver pressurized gas from gas supply assembly 140 to piston assembly 130.

Plug bolt 126 of valve assembly 120 is a generally hollow component that surrounds and translates axially across valve body 122. As shown in FIG. 5, plug bolt 126 includes head 190 and platform 192 for supporting plug 128, as discussed further below. Plug bolt 126 also includes a plurality of spaced apart rims 194 that extend radially outwardly from platform 192 to accommodate airflow through plug bolt 126.

Figure 8:
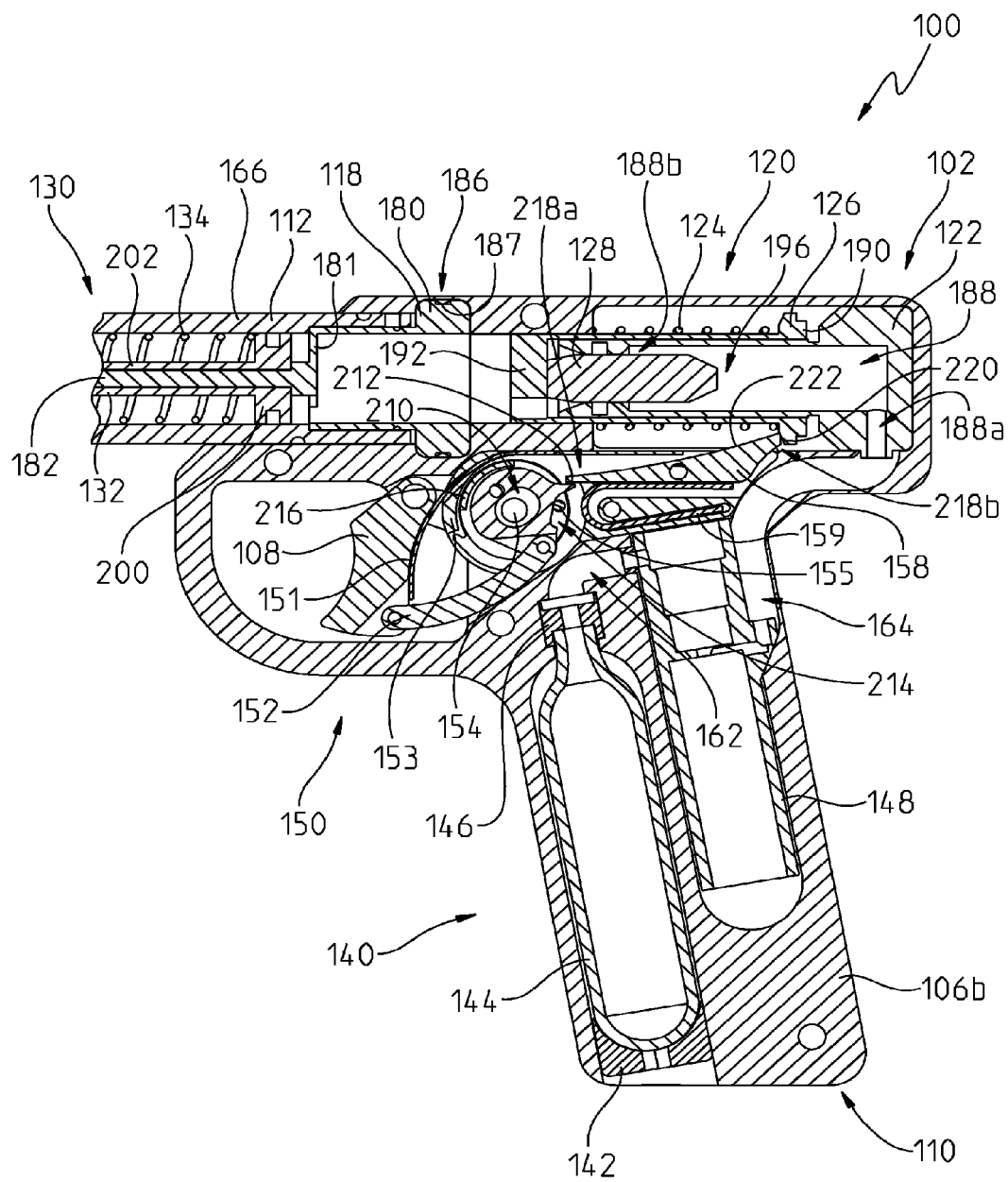
FIG. 8 is a cross-sectional view of a portion of the tool of FIG. 7.
Figure 9:
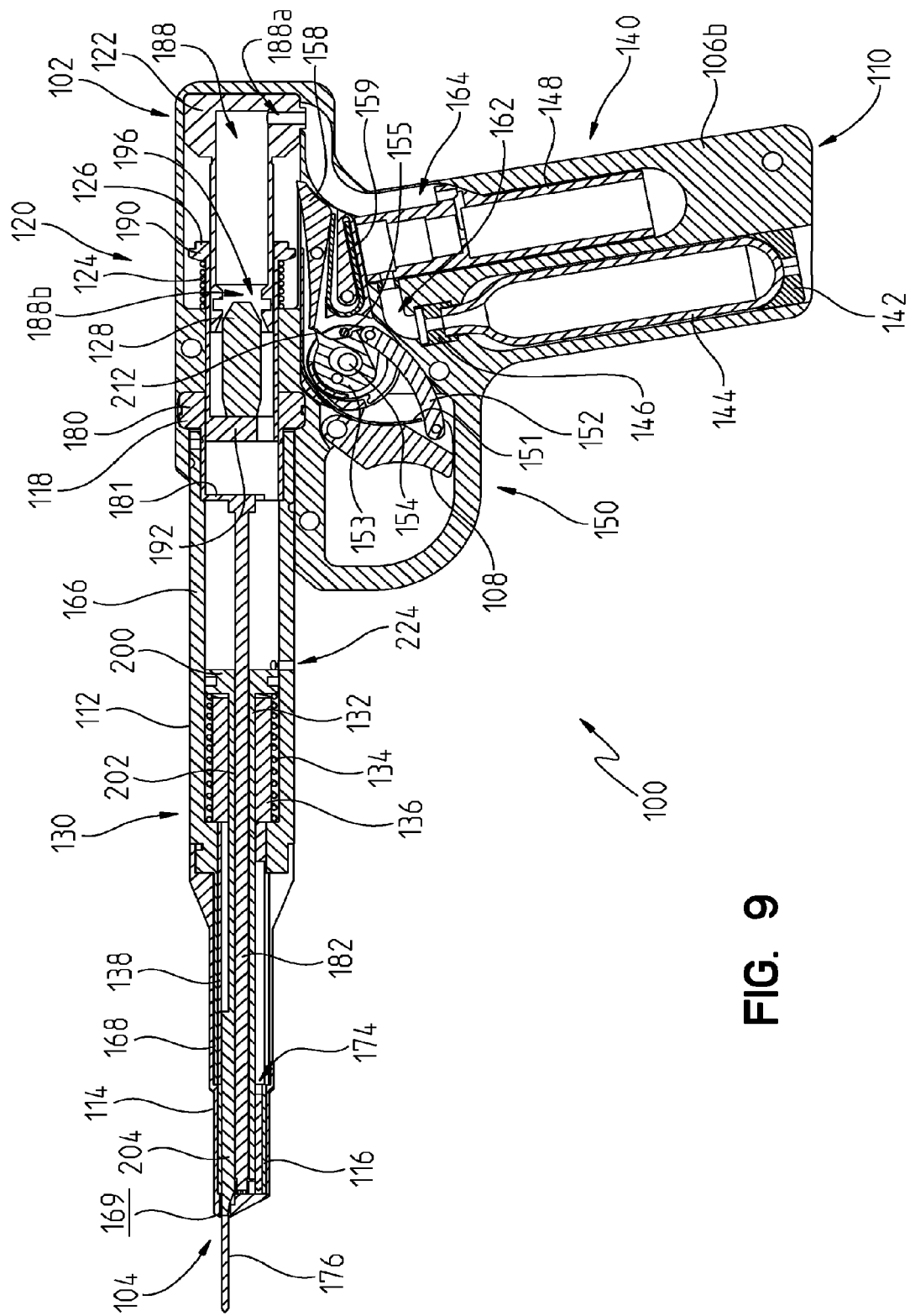
FIG. 9 is a cross-sectional view of the tool of FIG. 3 shown while being fired.

Plug 128 of valve assembly 120 is sized for receipt within outlet 188b of valve body 122, as shown in FIG. 7. Plug 128 translates axially relative to valve body 122 to close and open valve assembly 120. Valve assembly 120 closes when plug 128 seals outlet 188b of valve body 122 closed, as shown in FIG. 8, thereby preventing airflow from gas chamber 188 of valve body 122. Valve assembly 120 opens when tapered end 196 of plug 128 translates into outlet 188b of valve body 122 and opens outlet 188b, as shown in FIG. 9, thereby allowing pressurized gas to escape from gas chamber 188 of valve body 122.

Piston assembly 130 of tool 100 is received within barrel 112 and nose 114 and includes piston 132, piston return spring 134, damper 136, and guide 138, as shown in FIG. 4.

Piston 132 of piston assembly 130 is a cannulated component that translates axially within barrel 112. Piston 132 includes head 200, shaft 202, and a radially offset needle 204 that is coupled to shaft 202. Needle 204 is sized for receipt within each individual passageway 174 of cartridge 116. According to an exemplary embodiment of the present disclosure, passageways 174 of cartridge 116 are sized to limit needle 204 to axial movement therein, thereby stabilizing needle 204. As shown in FIG. 7, shaft 182 of dial 118 extends entirely through the cannulated piston 132 to reach cartridge 116. In operation, the surgeon rotates dial 118 to selectively align a desired passageway 174 of cartridge 116 with needle 204 of piston 132.

Damper 136 of piston assembly 130 is a cannulated component that is sized to receive shaft 202 of piston 132 therein, as shown in FIG. 4. Damper 136 may be constructed of plastic or rubber, for example, to resist and slow axial translation of piston 132.

Guide 138 of piston assembly 130 is a cannulated component that is sized and shaped to receive both shaft 202 and needle 204 of piston 132 therein, as shown in FIG. 5. Guide 138 may be contoured to closely match the outer profile of piston 132, thereby guiding and stabilizing axial translation of piston 132.

Gas supply assembly 140 of tool 100 is received within housings 106a, 106b, and includes cap 142, gas canister 144, puncture valve 146, and regulator 148. As shown in FIG. 6, cap 142 is removably coupled to housings 106a, 106b, for removing and replacing gas canister 144.

Gas canister 144 of gas supply assembly 140 contains a supply of pressurized gas. Preferably, gas canister 144 contains pressurized carbon dioxide gas ($CO_2$) or nitrogen gas (N2). Advantageously, gas canisters 144 are inexpensive, are readily commercially available, and are able to power tool 100 independently without any other secondary power source, such as a battery. Pressurized gas is generally commercially available in 12-gram supplies, although tool 100 may be designed to accommodate gas canisters 144 of various types and sizes. The pressure inside gas canister 144 may be as low as approximately 300 psi, 400 psi, 500 psi, or 600 psi, and as high as approximately 700 psi, 800 psi, 900 psi, 1000 psi, or more, although the pressure inside gas canister 144 will vary with temperature. A 12-gram supply of pressurized $CO_2$, for example, may have a pressure of about 850 psi at room temperature. When each new gas canister 144 is inserted into housings 106a, 106b, puncture valve 146 will open gas canister 144 to initiate airflow from gas canister 144 to regulator 148 via first gas channel 162, as shown in FIG. 6.

Regulator 148 of gas supply assembly 140 is provided to control the pressure of the gas that is delivered to valve assembly 120. When the pressure in valve body 122 of valve assembly 120 reaches a desired threshold, such as approximately 100 psi, 200 psi, 300 psi, 400 psi, 500 psi, or 600 psi, for example, regulator 148 cuts off the continued flow of pressurized gas to valve body 122. Therefore, even if the pressure in gas canister 144 fluctuates, regulator 148 is able to deliver pressurized gas to valve body 122 at a substantially constant pressure. Regulator 148 may be similar to those used in paintball guns, for example.

Trigger assembly 150 of tool 100 is received within housings 106a, 106b, and includes trigger 108, trigger spring 151, an arcuate linkage 152, rotating pawl 153, shaft 154, stop pin 155, left-side casing 156a, right-side casing 156b, left-side holder 157a, right-side holder 157b, seer 158, and a U-shaped seer spring 159, as shown in FIG. 6. Trigger 108 of trigger assembly 150 is pivotally coupled to housings 106a, 106b, to drive rotation of pawl 153, as discussed further below.

Pawl 153 of trigger assembly 150 includes an oblong central opening 210, an outwardly extending finger 212, and notch 214, as shown in FIG. 6. Shaft 154 extends through the oblong central opening 210 of pawl 153, such that pawl 153 is able to rotate about shaft 154 as well as translate relative to shaft 154. Pawl 153 may be at least partially covered by casings 156a, 156b, including guide arm 216 that protrudes from casing 156b.

Lock or seer 158 of trigger assembly 150 is pivotally coupled to housings 106a, 106b. Seer 158 includes first end 218a that contacts finger 212 of pawl 153 and second end 218b that contacts plug bolt 126 of valve assembly 120, as shown in FIG. 8. Second end 218b of seer 158 includes blocking surface 220 that faces proximal end 102 of tool 100 and ramped surface 222 that faces valve assembly 120 of tool 100.

Figure 10:
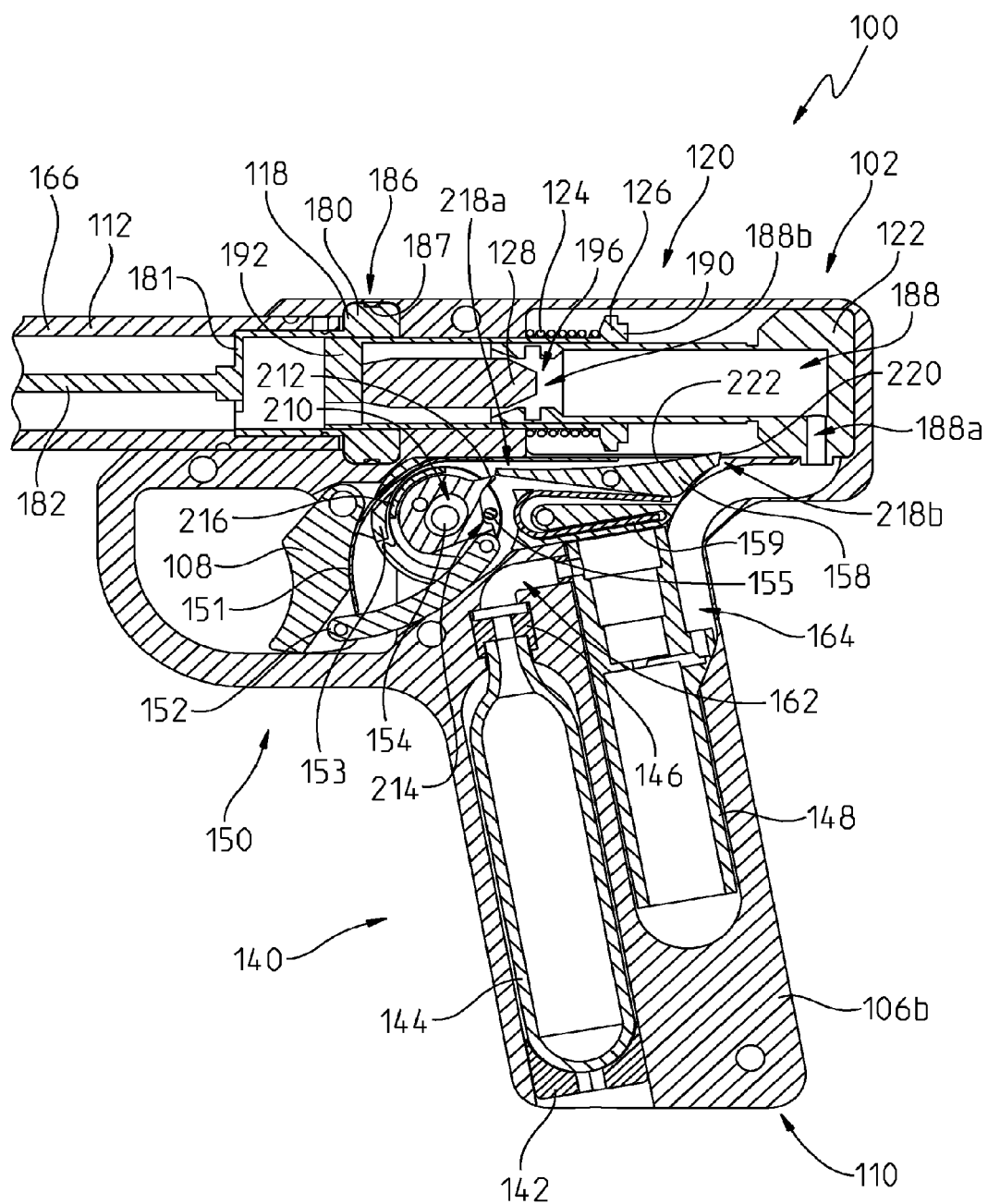
FIG. 10 is a cross-sectional view of a portion of the tool of FIG. 9.
Figure 11:
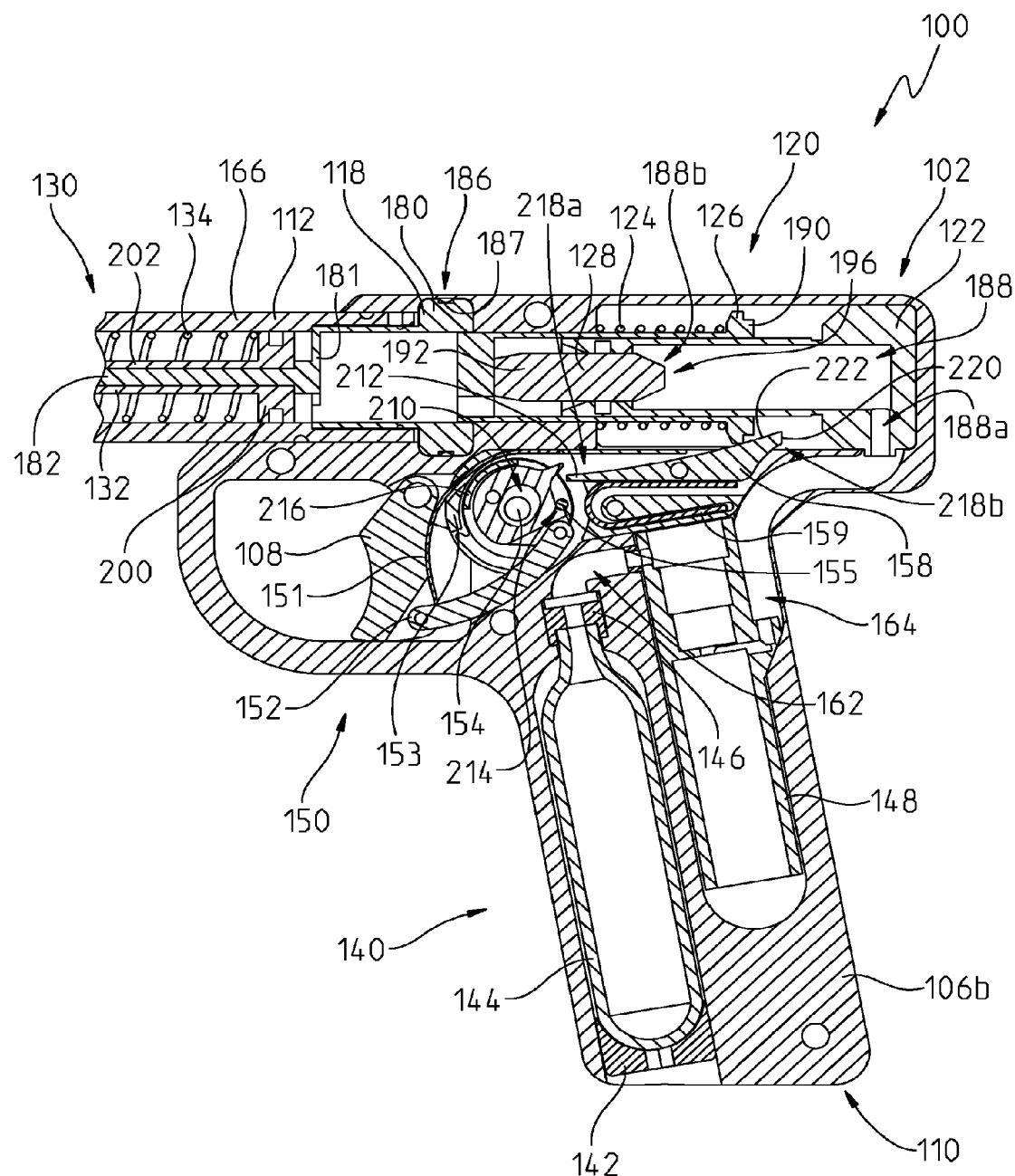
FIG. 11 is a cross-sectional view of a portion of the tool of FIG. 3 shown in an intermediate state after being fired.
Figure 12:
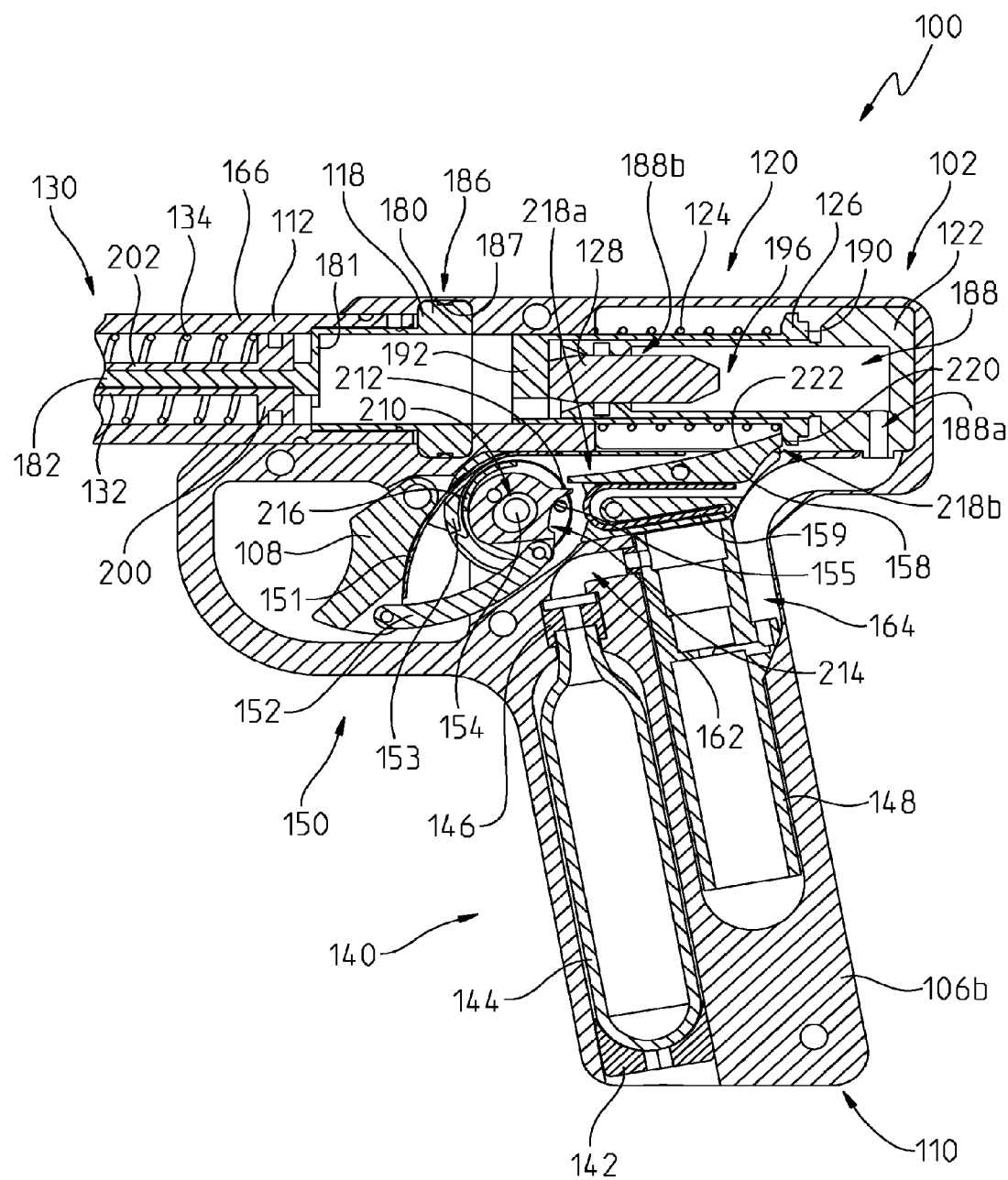
FIG. 12 is a cross-sectional view of a portion of the tool of FIG. 3 shown at rest after being fired.

The operation of tool 100 will now be described with reference to FIGS. 7-12. FIGS. 7 and 8 depict tool 100 at rest before being fired, FIGS. 9 and 10 depict tool 100 while being fired, FIG. 11 depicts tool 100 in an intermediate state after being fired, and FIG. 12 depicts tool 100 at rest after being fired.

With reference to FIGS. 7 and 8, tool 100 is shown at rest before being fired. In this state of rest, trigger 108 is biased outwardly under the force of trigger spring 151. Arcuate linkage 152 is coupled to trigger 108 and pulls finger 212 of pawl 153 downwardly and out of the way of seer 158. As shown in FIG. 8, seer 158 is biased upwardly under the force of seer spring 159, such that blocking surface 220 of seer 158 engages head 190 of plug bolt 126 to prevent plug bolt 126 from translating axially toward distal end 104 of tool 100.

Pressurized gas travels from gas canister 144 to regulator 148 via first gas channel 162 of housings 106a, 106b, and from regulator 148 into gas chamber 188 of valve body 122 via second gas channel 164 of housings 106a, 106b. However, pressurized gas is not able to escape from gas chamber 188 of valve body 122, because platform 192 of plug bolt 126 keeps plug 128 sealed within outlet 188b of valve body 122. Seer 158 prevents plug bolt 126, and in turn plug 128, from translating axially toward distal end 104 of tool 100 to escape from valve body 122.

Without the flow of pressurized gas from valve body 122, piston 132 retracts into tool 100 under the force of piston return spring 134, as shown in FIG. 7. Needle 204 of piston 132 is aligned with passageway 174 of cartridge 116 and pin 176 located therein, but is also retracted into tool 100 under the force of piston return spring 134.

With reference to FIGS. 9 and 10, tool 100 is shown while being fired. In this fired state, the surgeon pulls trigger 108 inwardly against the force of trigger spring 151. Arcuate linkage 152 forces finger 212 of pawl 153 to rotate upwardly, which causes first end 218a of seer 158 to pivot upwardly and second end 218b of seer 158 to pivot downwardly against the force of seer spring 159. Pivoting seer 158 in this manner moves blocking surface 220 of seer 158 away from plug bolt 126, thereby freeing plug bolt 126 to translate axially toward distal end 104 of tool 100, as shown in FIG. 10.

The elevated pressure in gas chamber 188 of valve body 122 forces plug bolt 126 and plug 128 axially toward distal end 104 of tool 100, which frees plug 128 from outlet 188b of valve body 122. As discussed above, this axial movement of plug bolt 126 is no longer blocked by seer 158. Pressurized gas escapes from outlet 188b of valve body 122 and flows around plug 128, through plug bolt 126, through head 180 of dial 118, and around shaft 182 of dial 118.

Pressurized gas then reaches head 200 of piston 132, which forces piston 132 to translate axially toward distal end 104 of tool 100 against the force of piston return spring 134, as shown in FIG. 9. This translating movement of piston 132 may be slowed by the presence of damper 136 around shaft 202 of piston 132 and may be guided and stabilized by the presence of guide 138 around shaft 202 and needle 204 of piston 132. In the fired position, needle 204 enters passageway 174 of cartridge 116 and drives pin 176 therefrom. With distal end 104 of tool 100 positioned against a fractured bone, the force against piston 132 may be sufficient to drive pin 176 into the bone for securing together adjacent bone fragments. For example, pin 176 may be driven through approximately 1 mm of cortical bone at pressures of about 70 psi and through approximately 4 mm of cortical bone at pressures between about 400 psi and 500 psi.

When head 200 of piston 132 is driven forward a sufficient distance to deliver pin 176, vent 224 in barrel 112 may be exposed, as shown in FIG. 9. Pressurized gas may escape from behind head 200 of piston 132 through vent 224, thereby reducing the pressure in tool 100. According to an exemplary embodiment of the present disclosure, vent 224 may direct pressurized gas radially outwardly from barrel 112 so as not to interfere with the patient situated near distal end 104 of tool 100 or the surgeon situated near proximal end 102 of tool 100.

With reference to FIG. 11, tool 100 is shown in an intermediate state after being fired. According to an exemplary embodiment of the present disclosure, tool 100 reaches this intermediate state automatically and rapidly after the fired state, even if the surgeon continues to pull trigger 108. Arcuate linkage 152 continues to force finger 212 of pawl 153 to rotate upwardly until stop pin 155 enters notch 214 of pawl 153, which limits further rotation of pawl 153. As shown in FIG. 11, finger 212 of pawl 153 rotates beyond first end 218a of seer 158, allowing seer 158 to return to its original starting position under the force of seer spring 159 with second end 218b of seer 158 extending back into the path of plug bolt 126.

After tool 100 is fired, the pressure in gas chamber 188 of valve body 122 drops because pressurized gas is able to escape through vent 224 (FIG. 9). Under this now-reduced pressure, valve return spring 124 is able to force plug bolt 126 and plug 128 back into outlet 188b of valve body 122 to shut off the supply of pressurized gas. Specifically, and as shown in FIG. 11, valve return spring 124 forces head 190 of plug bolt 126 over ramped surface 222 of seer 158, with plug bolt 126 carrying plug 128 back into outlet 188b of valve body 122.

Without the continued flow of pressurized gas from valve body 122, piston 132 retracts into tool 100 under the force of piston return spring 134, as shown in FIG. 11. Needle 204 (FIG. 7) of piston 132 also retracts into tool 100 under the force of piston return spring 134, leaving behind an empty passageway 174 of cartridge 116.

With reference to FIG. 12, tool 100 is shown at rest after being fired. According to an exemplary embodiment of the present disclosure, tool 100 reaches this rest state automatically and rapidly after the intermediate state, even if the surgeon continues to pull trigger 108. Due to the oblong shape of central opening 210 of pawl 153, pawl 153 translates downwardly over shaft 154. Finger 212 of pawl 153 also translates downwardly until reaching a position beneath first end 218a of seer 158 to await the next pull of trigger 108.

Valve return spring 124 continues to force plug bolt 126 and plug 128 back into outlet 188b of valve body 122 to shut off the supply of pressurized gas. Specifically, and as shown in FIG. 12, valve return spring 124 forces head 190 of plug bolt 126 over ramped surface 222 of seer 158 and, eventually, behind blocking surface 220 of seer 158. Once head 190 of plug bolt 126 is locked behind blocking surface 220 of seer 158, valve body 122 can only be reopened by pulling trigger 108 again.

Before firing tool 100 again, the surgeon may turn dial 118 to rotate cartridge 116. Rotating cartridge 116 will advance the next passageway 174 of cartridge 116, and pin 176 located therein, into alignment with needle 204.

Referring next to FIGS. 13-17, a portion of another exemplary handheld pneumatic tool 100' is provided for reducing and securing together bone fragments. Tool 100' of FIGS. 13-17 is similar to tool 100 of FIGS. 3-12, with like reference numerals indicating like elements, except as described below.

Figure 13:
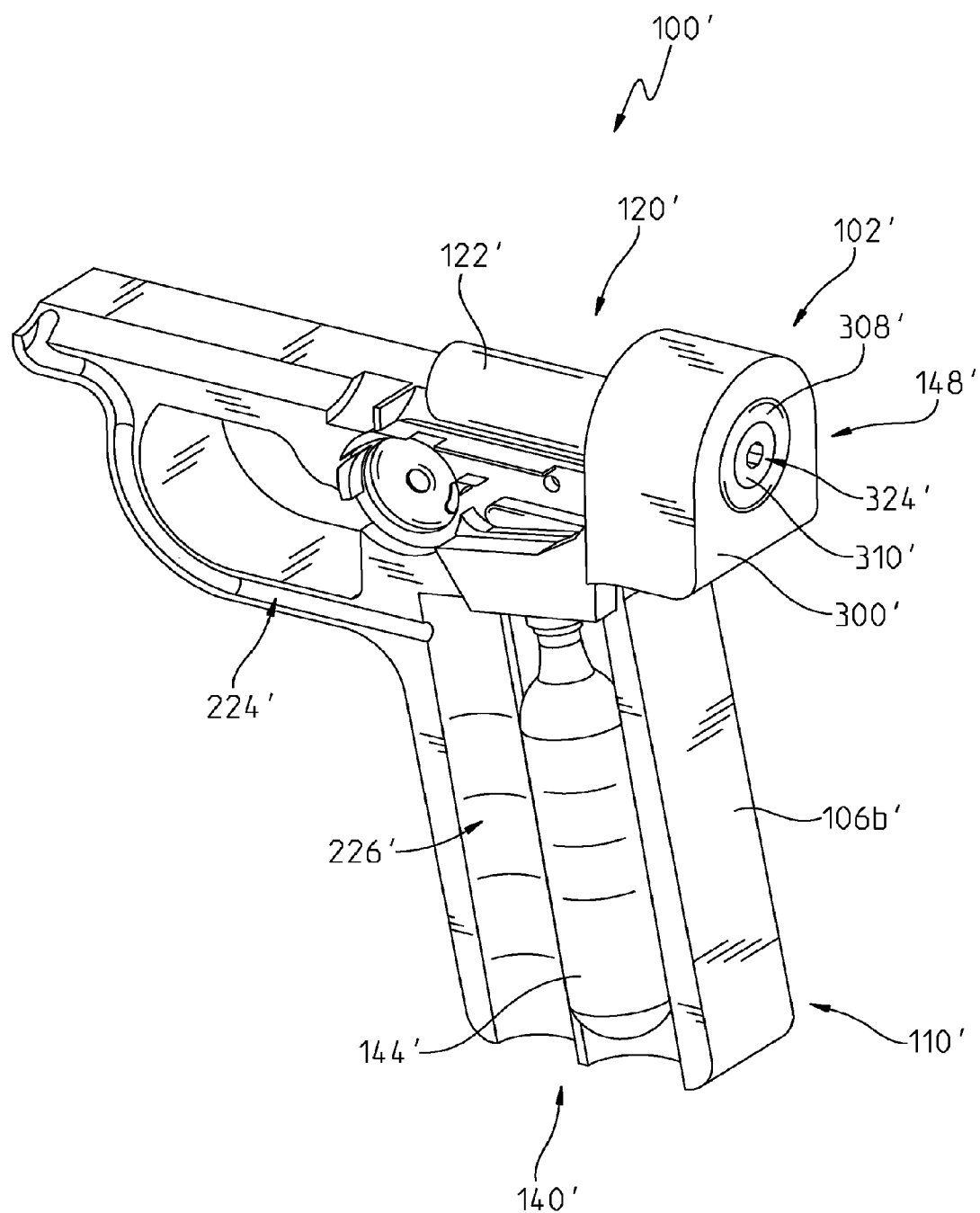
FIG. 13 is a perspective view of a portion of another exemplary tool of the present disclosure, the tool including a gas supply assembly having a regulator.

As shown in FIG. 13, proximal end 102' of tool 100' includes right-side housing 106b' that cooperates with a corresponding left-side housing (not shown) to support a suitable trigger assembly (not shown, but which may be similar to trigger assembly 150 of tool 100), piston assembly (not shown, but which may be similar to piston assembly 130 of tool 100), valve assembly 120' which includes valve body 122', and gas supply assembly 140' which includes gas canister 144' and regulator 148'. Housing 106b' defines gas channel 162' that connects gas canister 144' to regulator 148'. Housing 106b' also defines vent 224' and depressurization chamber 226' in handle 110'.

Figure 17:
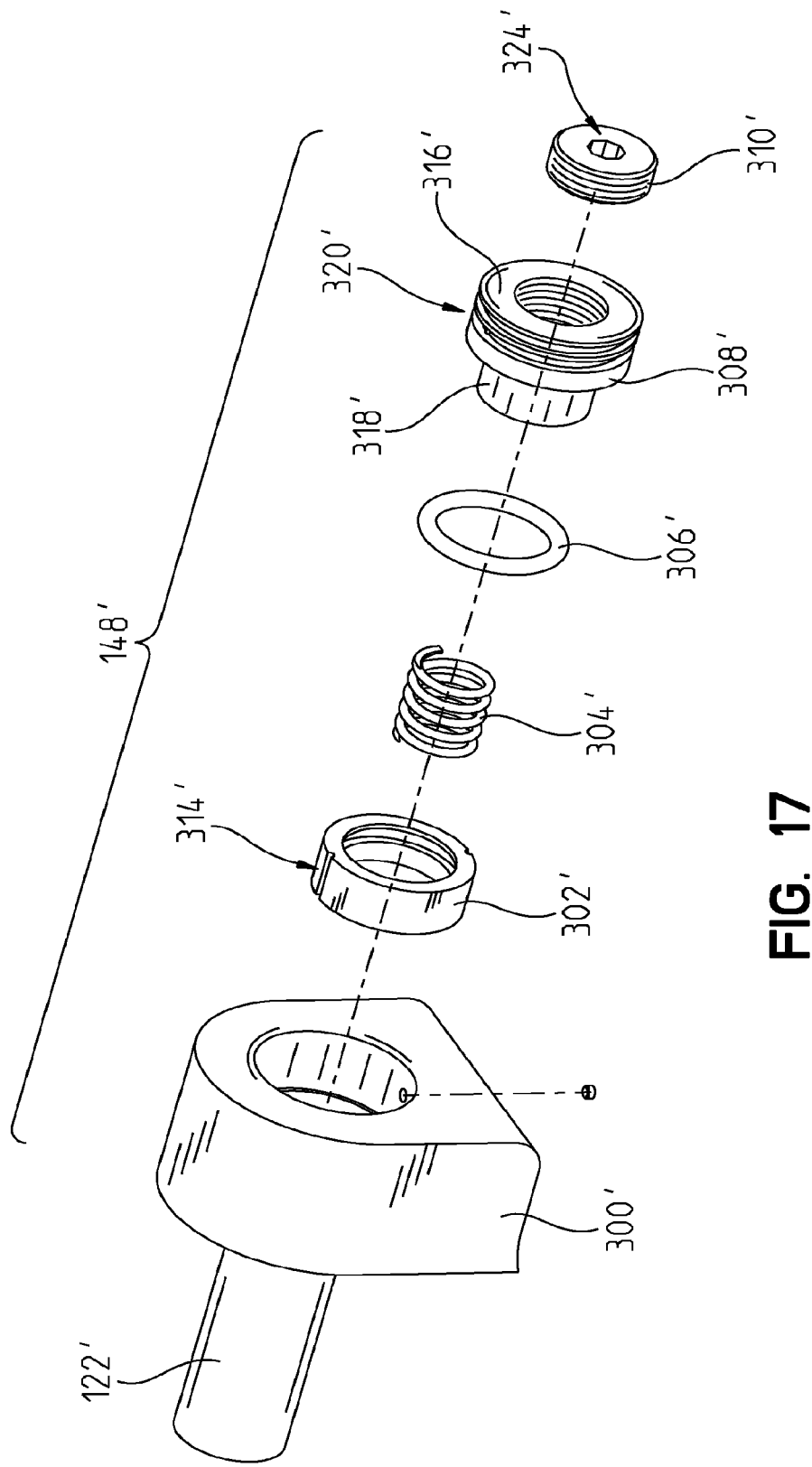
FIG. 17 is an exploded perspective view of the regulator of FIG. 13.

As shown in FIG. 17, regulator 148' of gas supply assembly 140' includes regulator body 300', diaphragm 302', actuator spring 304', seal 306', bolt 308', and selector 310'. Each component of regulator 148' is described further below.

Figure 14:
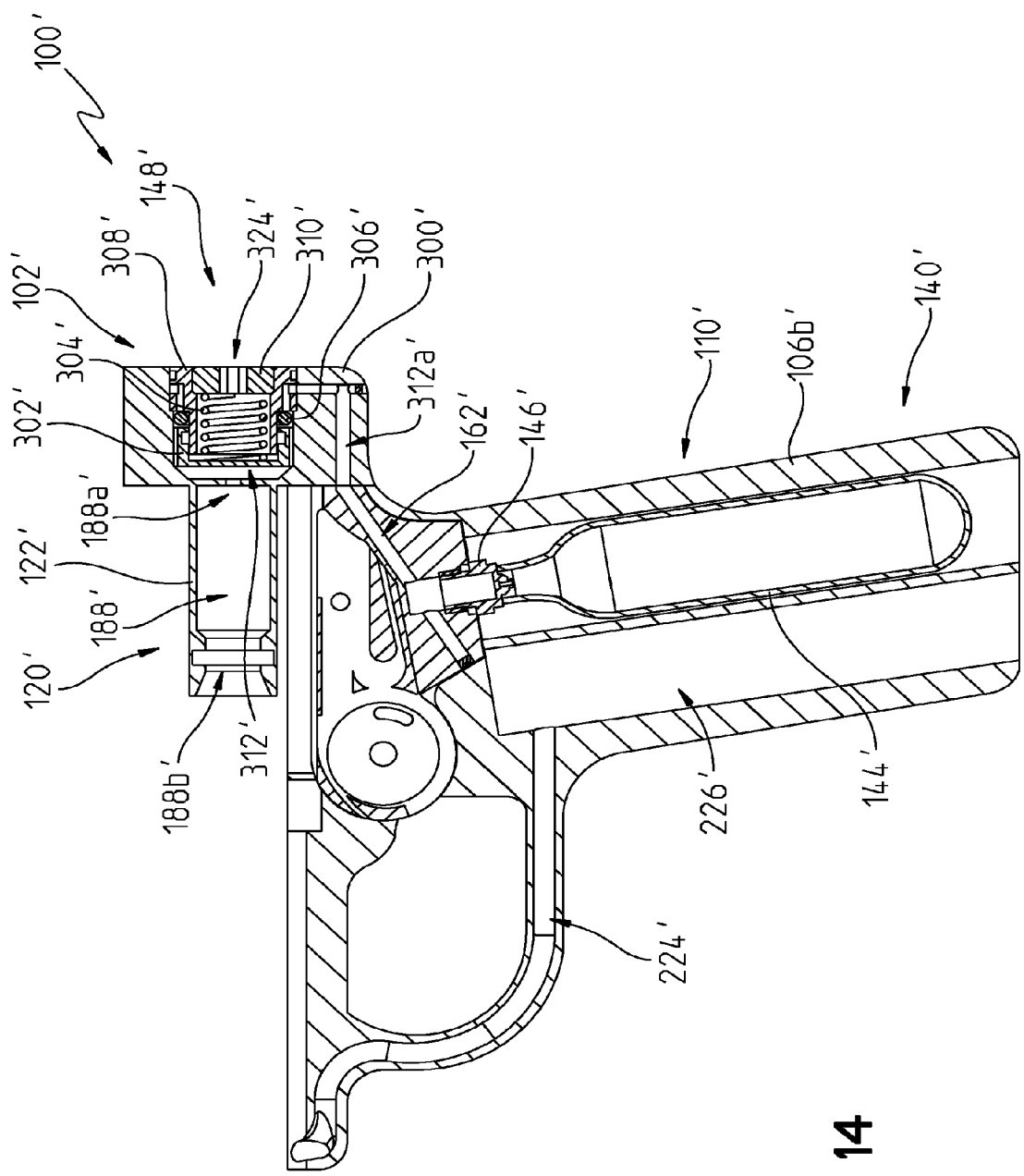
FIG. 14 is a cross-sectional view of the tool of FIG. 13.
Figure 15:
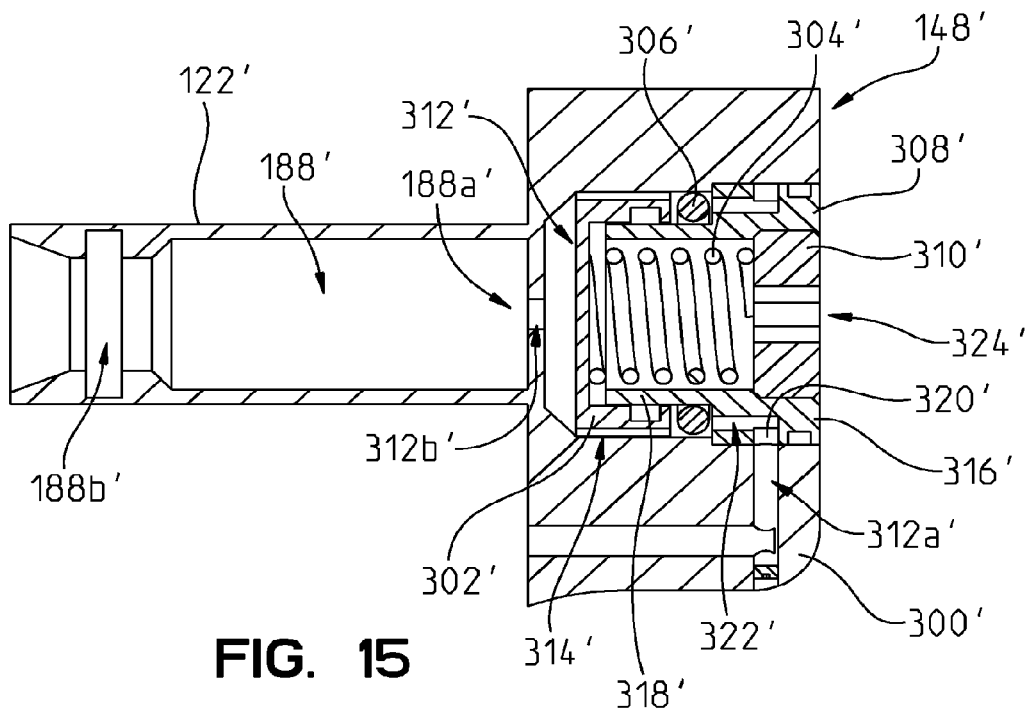
FIG. 15 is a cross-sectional view of the regulator of FIG. 13 shown in and open state.

Regulator body 300' of regulator 148' is a generally hollow component that defines gas chamber 312' therein, as shown in FIG. 15. Gas chamber 312' of regulator body 300' includes inlet 312a' that communicates with gas channel 162' of housing 106b' to receive pressurized gas from gas canister 144' (FIG. 14). Gas chamber 312' of regulator body 300' also includes outlet 312b' that communicates with valve body 122'. According to an exemplary embodiment of the present disclosure, regulator body 300' may be integrally formed with valve body 122', such that outlet 312b' of regulator body 300' defines or is directly connected to inlet 188a' of valve body 122'.

Diaphragm 302' of regulator 148' is sized for receipt within gas chamber 312' of regulator body 300' and is configured to translate axially therein. As shown in FIG. 17, diaphragm 302' defines one or more axial passageways 314' through regulator 148'.

Bolt 308' of regulator 148' is also sized for receipt within gas chamber 312' of regulator body 300'. Bolt 308' includes head 316' and shaft 318'. Head 316' of bolt 308' defines annular passageway 320' and one or more axial passageways 322' through regulator 148' Annular passageway 320' cooperates with each axial passageway 322' to define one or more L-shaped gas pathways through regulator 148'.

Selector 310' of regulator 148' is sized for receipt within bolt 308'. Selector 310' includes socket 324' that is configured to receive a suitable tool (not shown) for screwing selector 310' into bolt 308'. Selector 310' is configured to adjust the threshold pressure of regulator 148', and therefore the threshold pressure in valve body 122'. Tightening selector 310' into bolt 308' forces actuator spring 304' further out of bolt 308', which increases the threshold pressure in valve body 122'. Loosening selector 310' from bolt 308' allows actuator spring 304' to retract further into bolt 308', which decreases the threshold pressure in valve body 122'.

Figure 16:
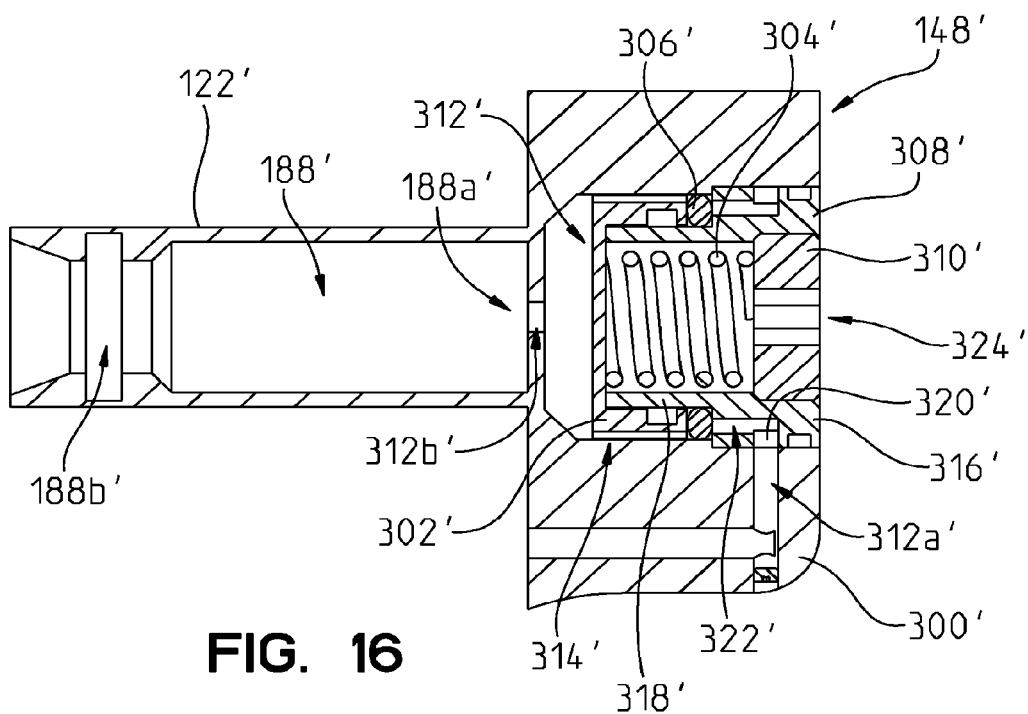
FIG. 16 is a cross-sectional view of the regulator of FIG. 13 shown in a closed state.

The operation of tool 100' is described with reference to FIGS. 14-16. Pressurized gas flows from gas canister 144' to inlet 312a' of regulator body 300' via gas channel 162', as shown in FIG. 14. Pressurized gas then flows through annular passageway 320' and axial passageways 322' of bolt 308' toward diaphragm 302'. Initially, actuator spring 304' forces diaphragm 302' apart from bolt 308', as show in FIG. 15, so that pressurized gas is able to flow around seal 306', through axial passageways 314' of diaphragm 302', and into valve body 122'. Over time, as pressurized gas continues to enter valve body 122', the pressure at outlet 312b' of regulator body 300' and inlet 188a' of valve body 122' increases, forcing diaphragm 302' toward bolt 308' against the force of actuator spring 304'. Eventually, when a threshold pressure is reached, seal 306' becomes sufficiently compressed to block axial passageways 314' of diaphragm 302', as shown in FIG. 16. At this stage, regulator 148' stops the continued flow of pressurized gas to inlet 188a' of valve body 122', thereby limiting the pressure in valve body 122'.

When the surgeon operates the trigger assembly of tool 100' (not shown, but which may be similar to trigger assembly 150 of tool 100), the pressurized gas is able to escape from outlet 188b' of valve body 122'. For example, operating the trigger assembly of tool 100' may free a bolt (not shown, but which may be similar to bolt 128 of tool 100) from outlet 312b' of regulator body 300'. The pressurized gas that escapes valve body 122' may pneumatically deliver a pin (not shown, but which may be similar to pin 176 of tool 100) into the patient's bone.

After delivering the pin, pressurized gas may escape through vent 224' in handle 110', as shown in FIG. 14, thereby reducing the pressure in tool 100'. The pressure of the escaping gas may be reduced in depressurization chamber 226' before the gas ever exits handle 110'. According to an exemplary embodiment of the present disclosure, vent 224' and depressurization chamber 226' may direct the escaping gas downwardly from handle 110' so as not to interfere with the patient or the surgeon holding handle 110'.

While this invention has been described as having preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A tool for stabilizing a fractured bone, comprising: a barrel having a proximal end and a distal end, the distal end of the barrel including a passageway for receiving a bone pin configured to be driven into the fractured bone to stabilize the fractured bone, the passageway being sized to accommodate axial movement of the bone pin through the passageway while limiting radial movement of the bone pin in the passageway; a piston having a proximal end and a distal end and configured to translate axially relative to the barrel, the proximal end of the piston including a head and the distal end of the piston including a needle formation sized for receipt within the passageway of the barrel; a cartridge for receiving the bone pin, the cartridge configured to be supported at the distal end of the barrel, wherein the cartridge includes an at least partially cylindrical body having an outer surface sized to fit within a nose portion at the distal end of the barrel, and an inner surface at least partly defining at least one passageway for receiving the bone pin; and a dial coupled to the tool for rotating the cartridge to selectively align the at least one passageway with the needle formation, wherein the needle formation configured to apply sufficient force to the bone pin to drive the bone pin axially from the barrel and into the fractured bone.

2. The tool of claim 1, wherein the piston is axially translatable within the barrel.

3. The tool of claim 1, wherein the barrel comprises a single passageway for receiving a single bone pin configured to be driven into the fractured bone to stabilize the fractured bone.

4. The tool of claim 1, further comprising a pressurized gas source for supplying a pneumatic force to the head of the piston to axially translate the piston relative to the barrel.

5. The tool of claim 4, further comprising a handle configured to receive the pressurized gas source.

6. The tool of claim 5, wherein the handle comprises a cylindrical recess, sized to receive the pressurized gas source, and extending through at least a portion of the handle.

7. The tool of claim 5, further comprising a gas connection port provided within the handle to which the pressurized gas source can be coupled.

8. The tool of claim 5, wherein the handle is configured to be coupled to the barrel.

9. The tool of claim 4, further comprising a puncture device operable to release gas from the pressurized gas source.

10. The tool of claim 4, further comprising a trigger assembly to release the piston.

11. The tool of claim 10, wherein the trigger assembly comprises a component that is movable transversely relative to the piston in response to operation of the trigger assembly to permit and restrain axial translation of the piston.

12. The tool of claim 10, wherein the pressurized gas source is configured to supply pneumatic force to the head of the piston both when the piston is restrained by the trigger assembly, and when driving the bone pin into the fractured bone.

13. The tool of claim 10, further comprising a pressurized volume for holding gas released by the pressurized gas source under pressure while the piston is restrained by the trigger assembly.

\* \* \* \* \*